(12) United States Patent
Tran et al.

(10) Patent No.: US 12,722,003 B1
(45) Date of Patent: Sep. 1, 2026

(54) APPARATUS, SYSTEM, AND METHODS FOR GENERATING ELECTRICAL FIELD THERAPY (EFT) VOLTAGES

(71) Applicants: Thang Viet Tran, Ho Chi Minh (VN); Tan Minh Tran, Ho Chi Minh (VN); Y Nhu Nguyen, Ho Chi Minh (VN); Hien Thi Nguyen, Ho Chi Minh (VN)

(72) Inventors: Thang Viet Tran, Ho Chi Minh (VN); Tan Minh Tran, Ho Chi Minh (VN); Y Nhu Nguyen, Ho Chi Minh (VN); Hien Thi Nguyen, Ho Chi Minh (VN)

(73) Assignee: NGUYEN TAT THANH UNIVERSITY, Ho Chi Minh (VN)

( * ) Notice: Subject to any disclaimer, the term of this patent is extended or adjusted under 35 U.S.C. 154(b) by 0 days.

(21) Appl. No.: 19/408,500

(22) Filed: Dec. 4, 2025

(51) Int. Cl.
*A61N 1/36* (2006.01)
*A61N 1/02* (2006.01)

(52) U.S. Cl.
CPC ......... *A61N 1/36021* (2013.01); *A61N 1/025* (2013.01); *A61N 1/36034* (2017.08)

(58) Field of Classification Search
CPC . A61N 1/36021; A61N 1/025; A61N 1/36034
See application file for complete search history.

(56) References Cited

U.S. PATENT DOCUMENTS

2022/0080191 A1* 3/2022 Gundert ............. A61B 18/1233
2024/0139504 A1* 5/2024 Travers ................ A61N 1/0476
2025/0229084 A1* 7/2025 Shen ...................... A61N 1/025

* cited by examiner

*Primary Examiner* — Carl H Layno
*Assistant Examiner* — Bryan Mcallister Lee

(57) ABSTRACT

An electrical field therapeutic (EFT) device is disclosed. The EFT device includes selector for selecting a voltage level including either an IF voltage or high voltages with a predetermined signal type and a treatment duration, a generator for generating the IF signal if the IF voltage is selected; a first transformer for transforming an AC wall outlet voltage into a plurality of low voltages if the high voltages are selected; a device for transforming the plurality of low voltages into the predetermined signal type; and a third transformer for transforming the low voltage with the predetermined signal type into the high voltage of the predetermined signal type.

20 Claims, 24 Drawing Sheets

FIG. 1 (PRIOR-ART)

FIG. 3 (PRIOR-ART)

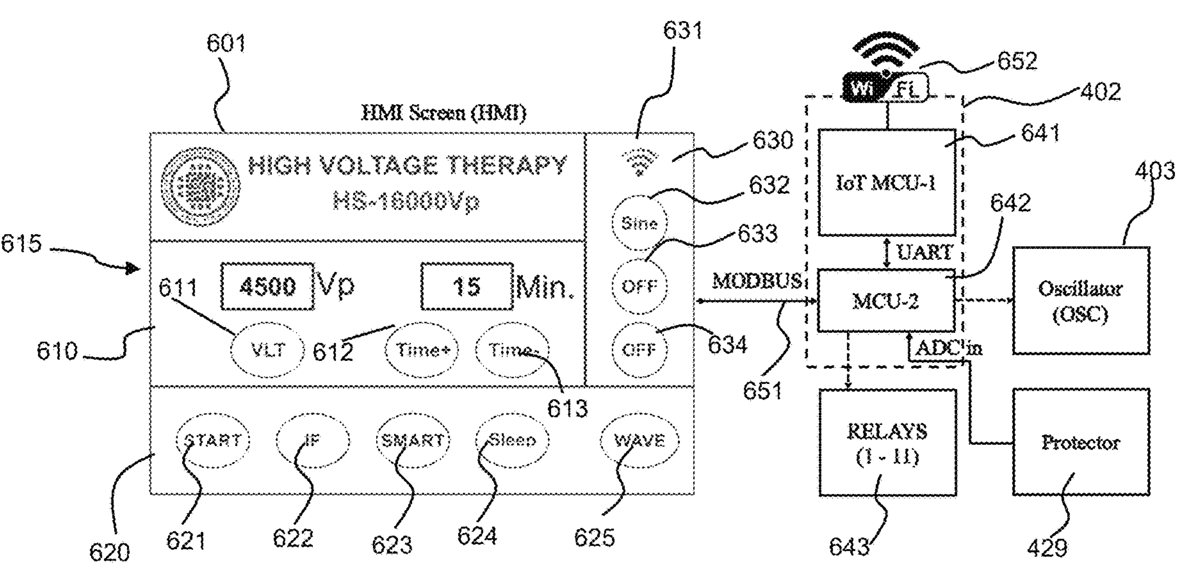
FIG. 6

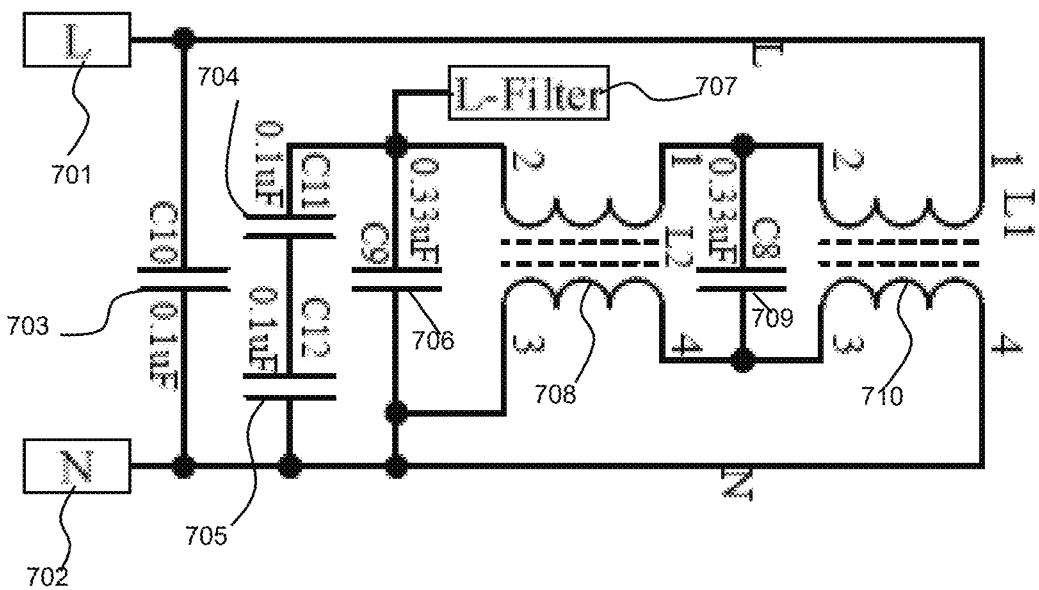
FIG. 7

APPARATUS, SYSTEM, AND METHODS FOR GENERATING ELECTRICAL FIELD THERAPY (EFT) VOLTAGES

FIELD OF THE INVENTION

The present invention relates generally to a medical device. Specifically, the present invention refers to a system and apparatus for generating different electrical field therapy (EFT) voltages for different health treatments.

BACKGROUND ART

Electric fields (EF) have been used in medicine for a long time [1]. Static electric fields have been shown to improve rheumatoid arthritis [2]. Pulsed electric fields are now considered an effective treatment for some types of cancer, based on the principle of electroporation. Pulsed electric field-based electroporation creates nano-sized defects in cancer cells. If the pulse rate is at a certain level, it causes cellular damage. These cellular defects cannot be repaired and cancerous cells are killed. This phenomenon is called irreversible electroporation (IRE). Conversely, short electrical pulses temporarily create pores in cell membranes, allowing the entry of molecules that would otherwise cannot pass through. After a short period of time, the pores close and the cell remains alive. This is called reversible electroporation. Irreversible electroporation (IRE) is used as a short-term surgical method, and can be used on tumors near large blood vessels [3] because it causes less damage to the surrounding area, while reversible electroporation helps transport drugs and molecules into the cell. This reversible electroporation is fundamental to electro chemotherapy.

Several studies on the effects of electric fields on animals have also shown significant potential for human applications. Preclinical studies have shown that exogenous electric fields are useful in repairing nerve injury [5]. Nanosecond pulsed electric fields reduce blood flow to tumors in mice [6]. In mice, it shows that high electric fields increase the penetration of DNA into cells.

High voltage electric field therapy are used to improve health problems. In the past 10 years, many studies have achieved outstanding results. From there, standards for electric field therapy have also been formed. Specifically, according to the American health organization standards in electric field therapy (EFT), the therapeutic voltages should not be greater than 18 kV, which corresponds to a current of no more than 5 mA flowing through a living body.

Dr. Toshikazu Shinba and colleagues conducted a study whose results show that electric field therapy (EFT) can alleviate pains originating from peripheral neuropathy and arthritis [8]. A total of 7 women aged 40 to 72 (mean±standard deviation=53.0±10.9) suffering from undiagnosed health problems were selected as study subjects. The levels of pain, insomnia, waking up at midnight, waking up early, tinnitus, dizziness, nausea, fatigue, and loss of appetite were assessed using the visual analog scale (VAS). In this VAS, the most severe condition has a maximum score of 100 before and after treatment.

Electromagnetic field therapy was performed using the Healthtron HES-A30 machine with a voltage of 30 kV alternating current at a frequency of 60 Hz. FIG. 1 shows graphs 100 for pain and insomnia before (pre) and after (post) treatment. Clearly, after treatments, pain and insomnia improved in the majority of patients. This study reinforces the potential of electrotherapy in the treatment of insomnia. In comparison, even though drug treatment is the most effective treatment for insomia, this method has side effects, even addiction. Its effectiveness gradually decreases over time [9].

In another attempt, a group of Professors including Takashi Ohtsuki, Tomoyuki Nabeta, Hiromoto Nakanishi, Hirohisa Kawahata, Toshio Ogihara and colleagues (Graduate School of Health Sciences, Morinomiya University School of Medicine, 1-26-16, Nankokita, Suminoe-ku, Osaka 559-8611, Japan) investigated the treatment of sleep disorders using electric fields [10]. The trial was conducted on a group of 19 university students with sleep disorders. These sleep disorders were defined as a score of 8 or higher on the Pitzburg Sleep Quality Index (PSQ) and divided into two groups. One group was undergone electric field (EF) intervention and another group was under a sham EF intervention (Control-C). The intervention group was exposed to EF source with frequency of 50 Hz, 18,000V and performed for 30 minutes per day for five consecutive days. The results of the treatment showed the ability to improve up to 89% of the patients' nocturnal sleep disorders as shown in the statistics in Table 1 below.

TABLE 1

Results of Improving Nocturnal insomnia. Comparison between EF Therapy and Natural Methods [9]

| Index | Group | Improvement (*) | Improvement (—) No. of Subjects | % Improvement | P |
|---|---|---|---|---|---|
| Total Time | EF | 4 | 5 | 44% | 0.26 |
| Sleep | C | 7 | 3 | 70% | |
| Time | EF | 8 | 1 | 89% | 0.07 |
| Wake Up at Midnight | C | 5 | 5 | 50% | |
| Deep | EF | 6 | 3 | 67% | 0.76 |
| Sleep Duration. | C | 6 | 4 | 60% | |

In another attempt, a group of scientists consisted of Yuzo Nakagawa-Yagi, Hiroyuki Hara, Takayo Akikuni Hara and colleagues (Hakuju Institute of Health Science, Address: 37-5 Tomigaya 1-chome, Shibuya-ku, Tokyo 151-0063, Japan) have scientifically tested the therapeutic effects of EF on chronic pain of unknown origin as well as in the treatment of insomnia and some other chronic diseases [11]. In FIG. 2, the research team conducted a study on the effects of 90 kV EF at 50 Hz applied to the human body for 30 minutes on N-acyl chains (N-acyl SERs). The study used selected response monitoring (SRM) analysis in plasma samples obtained from healthy subjects before and after a single treatment. The N-18:1 SER and N-16:0 SER components were significantly upregulated after exposure to EF as shown in FIG. 2 and FIG. 3.

The results of the electric field effects on the N-acyl SER components showed: (1) Pain alleviation mechanism through the binding of TRPV1 by N-18:1 SER, or N-16:0 SER components; (2) TRPV1-mediated calcium transmission in skeletal muscle hypertrophy. Although EF treatment was not repeated many times in this study, it can be seen that the ability of EF to improve skeletal muscle atrophy during aging; (3) the improved EA N-16:0 component has an effect in the treatment of colitis in ulcerative colitis through a mechanism of activating the PPAR-alpha dependent receptor 4 (TLR4) component. It is noted that N-acyl SER (serine) is an N-cyl amino acid. TRPV1 is a non-selective cation channel and polymodal receptor that is activated by capsaicin, endogenous lipids, heat, and mildly acidic pH. It triggers a cascade of events that lead to the transmission of pain signals, making it a potential target for pain management.

The results of the electric field effects on TRPV1 components showed: (1) Pain alleviation mechanism through the binding of TRPV1 by N-18:1 SER, or N-16:0 SER components; (2) TRPV1-mediated calcium transmission in skeletal muscle hypertrophy. Although EF treatment was not repeated many times in this prior-art study, it can be seen that the ability of EF to improve skeletal muscle atrophy during aging.

The improved EA N-16:0 component has an effect in the treatment of colitis in ulcerative colitis through a mechanism of activating the PPAR-alpha dependent receptor 4 (TLR4) component. Balanced fenofibrate of about 200 mg/day induces a state of calm in patients and helps improve many benign symmetric hyperlipidemias (MSL stands for Multiple Symmetric Lipomatosis).

FIG. 3 shows that N-16: 0 EA has a neuroprotective effect in Alzheimer's disease. In addition, other ingredients also have the effect of improving memory and some other diseases. N-16:0 EA means Eugenol acetate which has a neuoprotective effect primarily for ischemic stroke.

A study on mice published on Aug. 2, 2012 in the journal Cell MetabolismFAS showed that the conversion of carbohydrates into fat in the body is related to the enzyme called fatty acid synthase (FAS) that synthesizes and regulates fat [12].

Fatty acid synthase (FAS) activity affects the activity of a protein called peroxisome proliferator activated receptor (PPAR) in two forms: PPAR-alpha, which helps burn brown fat, and PPAR-gamma, which helps accumulate white fat. Those mice without the FAS enzyme in their fat cells showed to have increased PPAR-alpha activity. This PPAR-alpha activity burns fat into heat. Those mice are not obese. Conversely, those mice with more FAS enzyme in their fat cells showed to have increased PPAR-gamma activity. This PPAR-gamma increases fat accumulation. As a result, these mice are obese. Another intermediate protein is Peroxisomal Reductase Activating PPAR-gamma (PexRAP) has the function of activating PPAR-gamma.

One study found that if PexRAP is blocked, fat accumulation is reduced because the activity of PPAR-gamma is also blocked. Dr. Irfan J Lodhi, the author of the study, concluded that whether or not mice become obese is not due to diet but due the enzyme FAS regulates the activity of PPAR. If PPAR-gamma activity increases, obesity will occur. Conversely, if PPAR-alpha activity increases, obesity will not occur.

Author Yasihiro Mitani and colleagues studied the muscle relaxation effect of high voltage electric field on 15 healthy men, age 25.4±5.4, height 172.3±6.0 cm, weight 67.9±12.4 kg (mean±standard deviation) [13]. The subjects were divided into 2 groups. One group was the control group and the other group was treated with 18 kV high voltage electric field for 30 minutes. Skin temperature, blood flow velocity, blood pressure, heart rate, muscle stiffness, and muscle relaxation were measured before and after the intervention. Subjects were then asked to perform self-stretching movements of the muscles. These included the trapezius, hamstrings, and rectus femoris, and muscle stiffness and stretch were also measured. The results showed that the electric field did not affect muscle stiffness or circulatory dynamics. However, the mechanism by which the high-voltage electric field improves muscle stretch ability remains unclear and requires further study.

Therefore, there are needs for a high-voltage electric field therapy device capable of generating various voltages so that the mechanism by which the electric field therapy effects on medical treatments can be verified.

two high-voltage sources up to 16,000 Vp at basic frequency 50 Hz/60 Hz (full wave and half wave) including NHV (Negative High Voltage) and PHV (Positive High Voltage) outputs and a 2,800V voltage source at frequency 70 KHz and IF (Intermediate Frequency) Output.

There are needs for a high-voltage electric field therapy device that can generate various therapeutic low voltage signals including 6.25V, 7.8V, 12V, 23.5V, 35V, 70V, 110V, 125V.

There are needs for a high-voltage electric field therapy device that can generate high voltage levels including 800V, 1,000V, 1,500V, 3,000V, 4,500V, 9,000V, 14,000V, and 16,000V.

There are needs for a high-voltage electric field therapy device with an Internet of Things controller (IoTCTR) operative to track all treatment information via the cloud server.

There exists needs for a high-voltage electric field therapy device that can retain treatment history, time of use, and technical problems helpful to the diagnosis and maintenance of the device.

The apparatus and system of the present invention solve the above problems and meet the market and research needs.

SUMMARY OF THE INVENTION

Accordingly, an object of the present invention is to provide a device that can generate various electrical voltages and retain the treatment results so that the effects of electric field therapy (EFT) on human diseases can be ascertained.

More particularly, another object of the present invention is to provide a high-voltage electric field therapy device capable of generating high-voltage sources up to 16000 Vp full wave and half wave at basic frequency 50 Hz/60 Hz including NHV Negative High Voltage (NHV) and Positive High Voltage (PHV) outputs; and a 2800V output voltage source at an intermediate frequency (IF) of 70 KHz.

Another object of the present invention is to disclose an electric field therapy device (the "device") including (a) means for selecting a voltage level including either an IF voltage or high voltages with a predetermined signal type and a treatment duration, (b) means for generating the IF signal when an IF voltage is selected; (c) means for transforming an AC wall outlet voltage into a plurality of low voltages when low voltages are selected; (d) means for transforming the plurality of low voltages into the predetermined signal types (regular, alpha, and beta signals); and (e) means for transforming the low voltage with the predetermined signal type into the high voltages of the predetermined signal type.

Another object of the present invention is to provide a device that uses an oscillator circuit (OSC) that generates sinusoidal signals which are amplified through a class B amplifier circuit and a high frequency transformer (HFT).

Another object of the present invention is to provide a device that uses wall outlet AC power sources of 110V/220V at 50 Hz/60 Hz to generate 8 different low voltages: 6.25V, 7.8V, 12V, 23.5V, 35V, 70V, 110V, 125V.

Another object of the present invention is to provide a device with an IoT controller that can select the required treatments with corresponding high voltage levels of 800V, 1,000V, 1,500V, 3,000V, 4,500V, 9,000V, 14,000V, 16,000V in 3 different directions, namely, 1) through relay circuit connected directly to the high voltage transformer (HVT) circuit and a protector circuit; 2) through the Lα inductor to deviate the standard sine signal and generate alpha waves and transfer to the HVT via the protection circuit; and 3) through RL9 to the Lβ inductor designed to deviate the standard sinusoidal signals into beta waves.

Another object of the present invention is to provide a device with a protector circuit is responsible for protecting the HVT circuit from surge power and overcurrent.

Another object of the present invention is to provide a device with an IoT controller (IoTCTR) that controls the relay and transformer circuits to issue specific medical treatment.

An object of the present invention is to provide a device that includes an IoT controller (IoTCTR) capable of tracking all information related to treatment techniques for different users via a Cloud Server.

Another object of the invention is to provide a device which includes a graphic user interface (GUI) on the Web platform and/or smart mobile devices, allowing users to monitor and evaluate the treatment process of the patients. In addition, the IoTCTR is also capable of tracking the time of use and all incidents to facilitate the repair and maintenance of the device.

Finally, an object of the present invention is to provide a device that includes an IoT controller (IoTCTR) capable of tracking the operation problems to facilitate the repair and maintenance of the device.

These and other advantages of the present invention will no doubt become obvious to those of ordinary skill in the art after having read the following detailed description of the preferred embodiments, which are illustrated in the various drawing and figures.

BRIEF DESCRIPTION OF THE DRAWINGS

The accompanying drawings, which are incorporated in and form a part of this specification, illustrate embodiments of the invention and, together with the description, explain the principles of the invention.

FIG. 6 shows a graphic user interface (GUI) of the HS-16000 Vp supported by IoT, Wifi network, relay network, oscillator (OSC), protector circuit, and controllers in accordance with an exemplary embodiment of the invention.

FIG. 7 shows a schematic diagram of a bandpass filter in accordance with an exemplary embodiment of the invention.

The above figures are for the purposes of illustration only. A person of ordinary skill in the art will readily recognize from the following discussion that alternative embodiments of the structures and methods illustrated herein may be employed without departing from the principles of the technology described herein.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Within the scope of the present description, the reference to "an embodiment" or "the embodiment" or "some embodiments" means that a particular feature, structure, or element described with reference to an embodiment is comprised in at least one embodiment of the described object. The sentences "in an embodiment," "in the embodiment," or "in some embodiments" in the description do not, therefore, necessarily refer to the same embodiment or embodiments. The features, structures, or elements can be furthermore combined in any adequate way in one or more embodiments.

Figure 1:
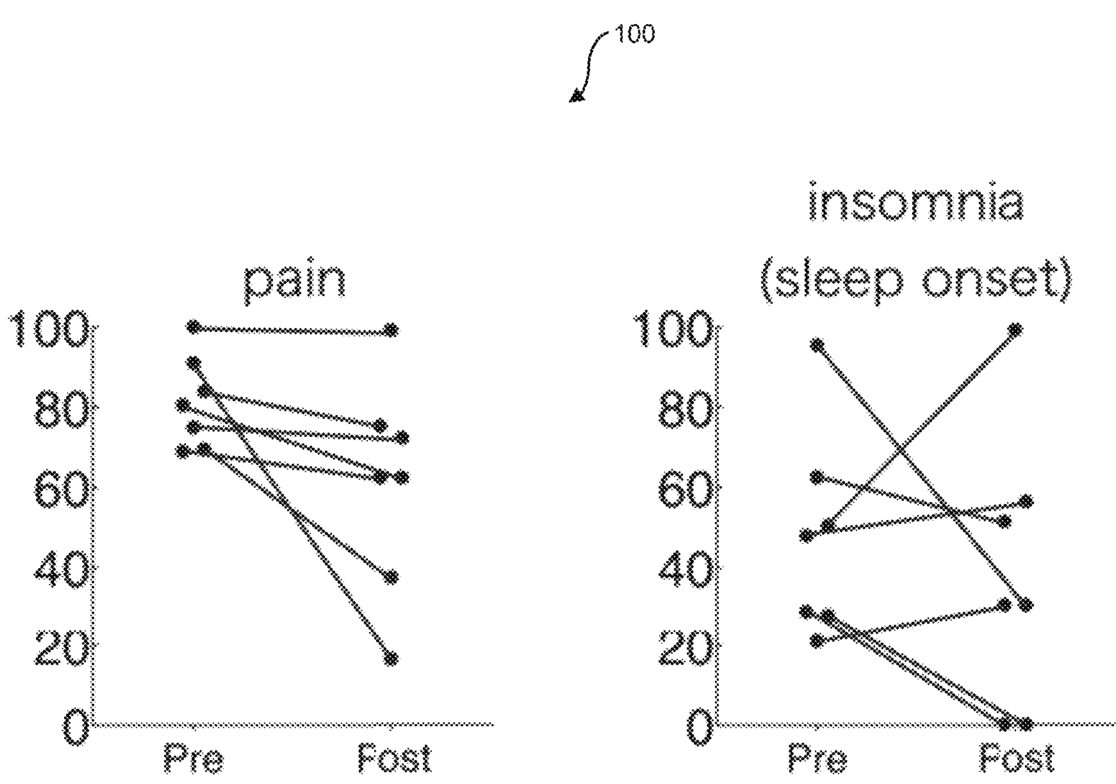
FIG. 1 presents prior-art graphs that show the effectiveness of electrophoresis using high voltages to treat pain and insomnia.
Figure 2:
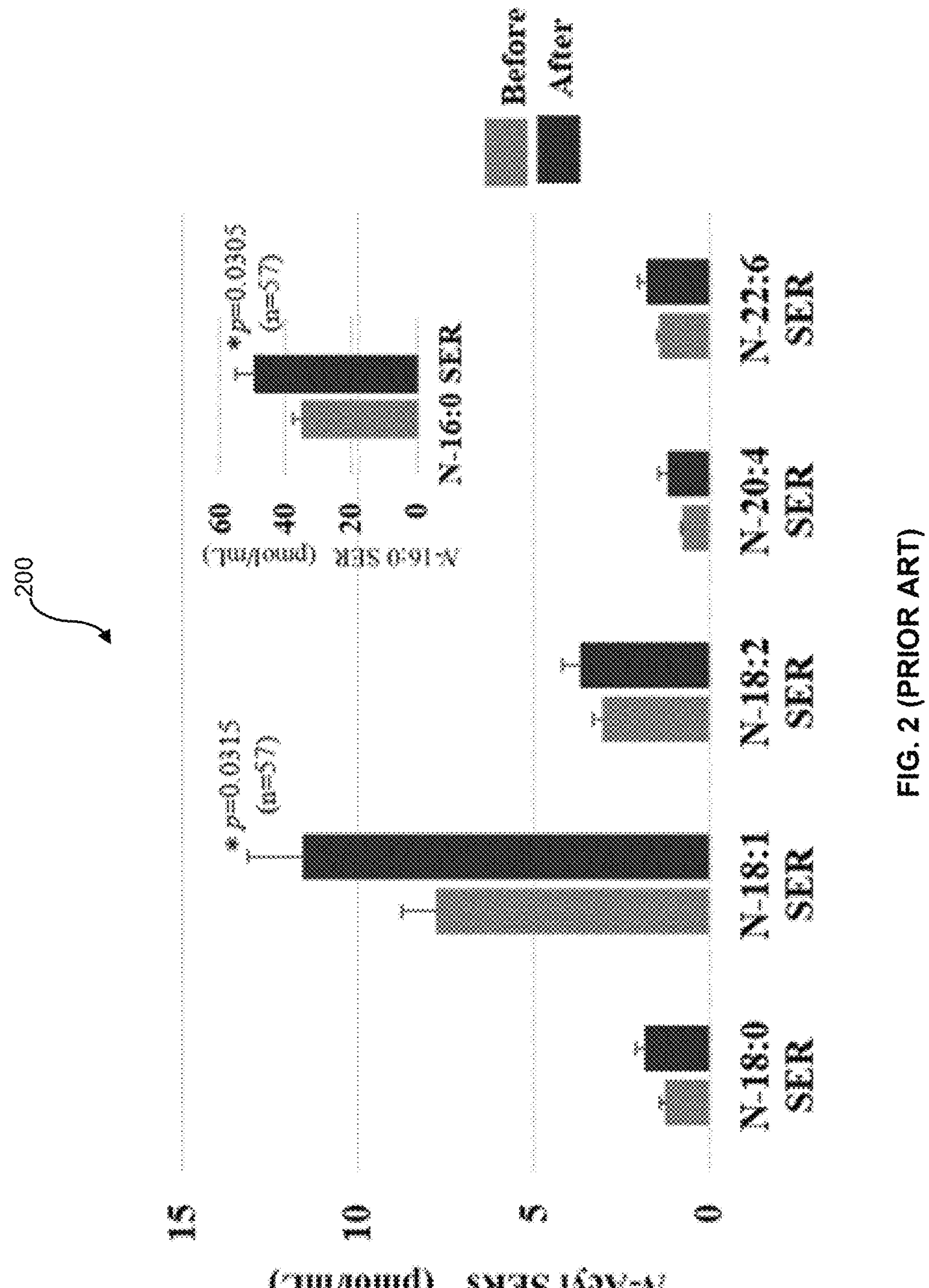
FIG. 2 shows a prior-art bar graph of the effects of contact high electrical voltages of 9 kV at 50 kHz for 30 minutes on N-acyl.
Figure 3:
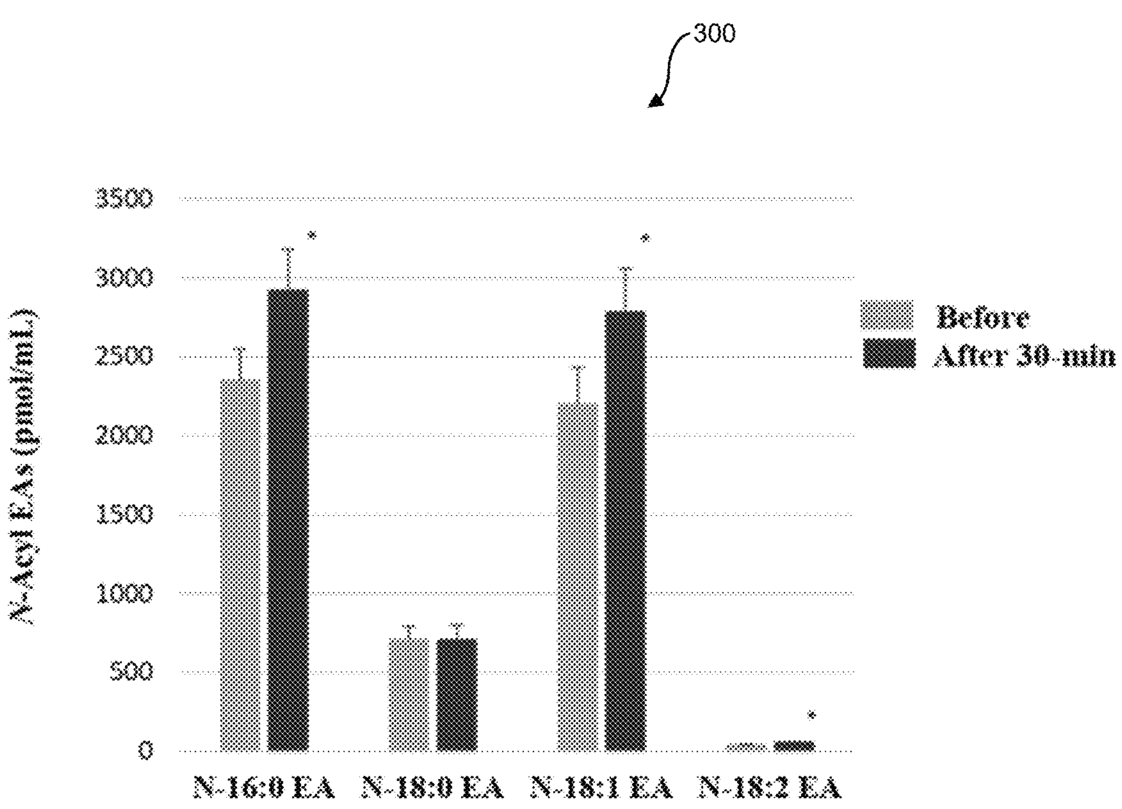
FIG. 3 shows a prior-art bar graph of the effects of contact high electrical voltages of 9 kV at 50 kHz for 30 minutes on N-acyl EAs in the plasma of healthy patients.
Figure 4:
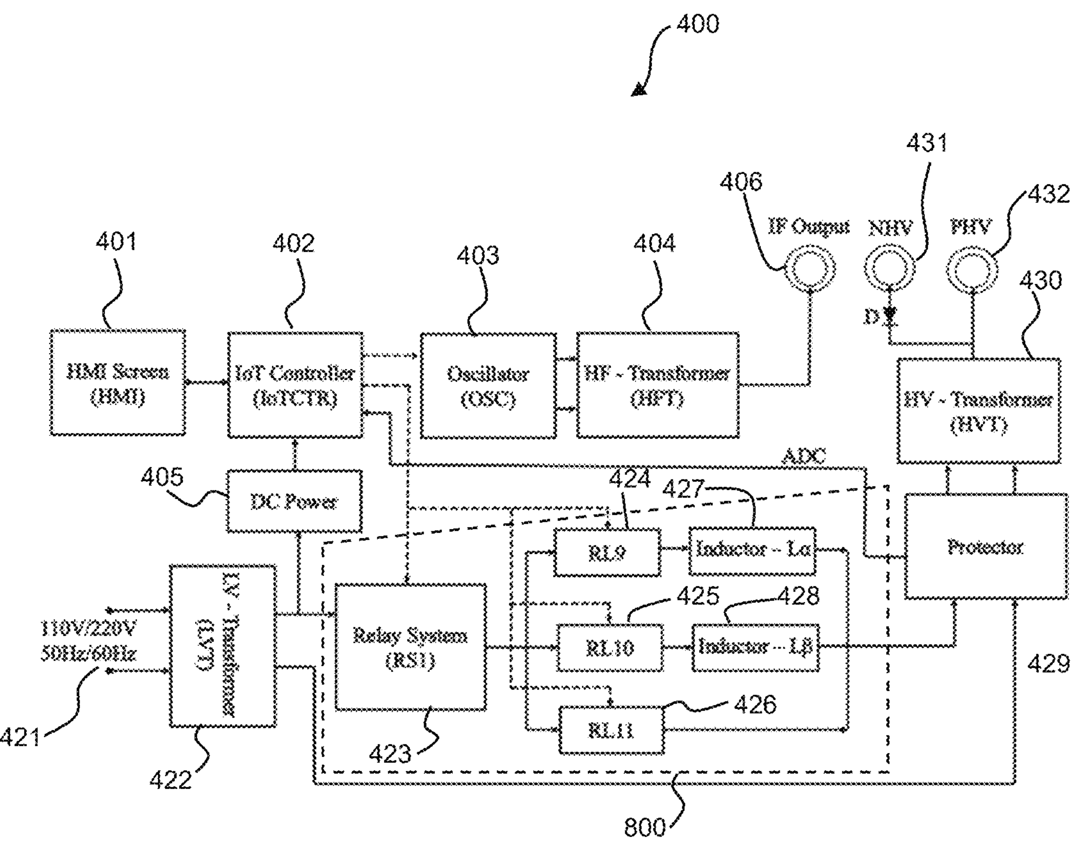
FIG. 4 shows an overview system block diagram of an HS-16000 Vp device for generating electrical field therapeutic (EFT) IF voltage and high voltages in accordance with an exemplary embodiment of the present invention.

According to FIG. 4, an overview system level block diagram of a HS-16000 Vp device 400 for generating electrical field therapeutic (EFT) IF voltage and high voltages in accordance with an exemplary embodiment of the present invention is illustrated. HS-16000 Vp device 400 includes a HMI screen 401, an IoT controller (IoTCTR) 402, an oscillator circuit (OSC) 403, an HF transformer (HFT) 404 connected to an IF output connector 406. HMI screen 401 communicates with IoTCTR 402 to display various control functions of HS-16000 Vp device 400. IoTCTR 402 controls OSC 403 which in turn outputs to HF transformer 404. In various embodiments of the present system, HF transformer 404 transforms the 70 kHz output from OSC 403 to the desired therapy voltage.

Continuing with FIG. 4, HS-16000 Vp device 400 also includes wall outlet voltage connector 421, a low voltage transformer (LVT) 422, a relay system (RS1) 423, a relay RL9 424, a relay RL10 425, and a relay RL11 426. Relay RL9 424 is connected to a first (alpha) inductor (Lα) 411 and relay RL10 425 is connected to a second (beta) inductor (Lβ) 428. LVT 422 and second inductor (Lβ) 428 output to a protector circuit 429. Protector circuit 429 protects and outputs to a high voltage transformer circuit (HVT) 430. HVT circuit 430 has two output connectors: a negative high voltage (NHV) output 431 and a positive high voltage (PHV) output 432. A DC power circuit 405 provides voltage supply to the entire HS-16000 Vp device 400. The output of LVT circuit 422 is protected by protector circuit 429 from overcurrent and damaging power surges. In return, protector circuit 429 outputs a digital signal. This digital signal, converted from analog signal from LVT circuit 422 by analog to digital converter (ADC), regulates IoTCTR 402.

In operation, users such as doctors or nurses enter a desire treatment voltage and therapy duration to HMI screen 401 for electroporation. These inputs are communicated to IoTCTR 402. Next, IoTCTR 402 activates OSC 403 to generate a sinusoidal signal. This sinusoidal signal is input to high voltage transformer (HFT) 404 for outputting an intermediate frequency high voltage output IF 406. Low voltage transformer (LVT) 422 receives 110V/220V at 50 Hz/60 Hz voltage from wall outlet connectors 421. These common wall outlet voltages go through relay system (RS1) 423, RL9 424, RL10 425, RL11 426, first inductor (Lα) 427 and second inductor (Lβ) 428. The amount of relay is set by users at HMI screen 401. The outputs of the relayed voltages go through protector circuit 429 and then to high voltage transformer (HVT) 430. These high voltages (800V-16,000 Vp) are used at NHV output 431 or PHV output 432. The detailed description of each circuit in HS-16000 Vp device 400 will be described in the following FIG. 5 to FIG. 21.

Figure 5:
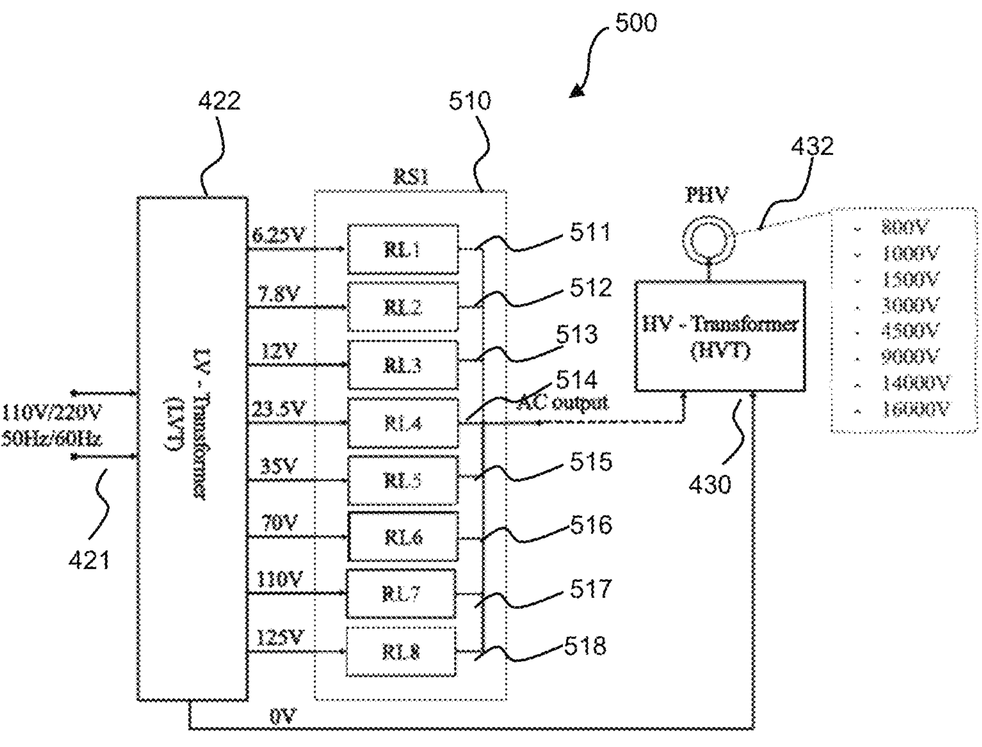
FIG. 5 shows a schematic diagram of a low voltage transformer (LVT) and high voltage transformer (HVT), and a relay network (RL) connected together to generate various high treatment voltages in accordance with an exemplary embodiment of the present invention.

Now referring to FIG. 5, a schematic diagram of a relay system (RS1) 500 according to an embodiment of the present invention is illustrated. LVT circuit 422 receives alternating current sources from wall outlet connector 421 at 110V/220V at 50 Hz/60 Hz. Low voltage transformer (LVT) 422 outputs eight different voltage levels, namely, 6.25V, 7.8V, 12V, 23.5V, 35V, 70V, 110V, and 125V. The 6.25V is input into RL1 511, 7.8V to RL2 512, 12V to RL3 513, 23.5V to RL4 514, 35V to RL5 515, 70V to RL6 516, 110V to RL7 517, and 125V to RL8 518. The ground voltage from LVT 422 is input to HVT 430. HVT 430 outputs the following high voltages 800V, 1,000V, 1,500V, 3,000V, 4,500V, 9,000V, 14,000V, and 16,000V at PHV 432.

Referring now to FIG. 6, a systematic diagram 600 of a graphic user interface (GUI) displayed on the HMI screen 401, the microprocessors, relay system, protector, and oscillator of the HS-16000 Vp device according to an embodiment of the invention is illustrated. 7-inch HMI screen 401 is a graphic user interface (GUI) that renders various sections on the human machine interface (HMI) screen 401. In various embodiments of the present invention, HMI screen 401 can be displayed on a smart phone (not shown), laptop (not shown), and/or desktop computer (not shown). HMI screen 401 includes a logo section 601, a voltage and time selection section 610, an initialization section 620, and a wave selection section 630.

Continuing with FIG. 6, voltage and time selection section 610 includes the following function buttons: a VLT (Voltage) button 611 allows changing the following therapeutic voltage levels: 4,500V, 9,000V, 14,000V and 16,000V. Each time VLT button 611 is pressed, the values will change and alternate from 16,000V to 4,500V. The voltage values are displayed on the rectangular frame above the VLT button 611. Time+ 612 and Time− buttons 613 change the treatment time from 0 minutes to 60 minutes. When Time+ button 613 is pressed, the treatment time duration is increased by 5 minutes interval. When Time− button 612 is selected, the treatment time period is decreased by 5 minutes. Both voltage and time values are displayed separately on a section 615.

A WAVE button 625 allows selecting either the PHV or NHV output therapy signal as Sine, Alpha, or Beta. Please refer to FIG. 21 for the descriptions of the wave types. The current treatment signal is activated by a Sine button 632, an OFF button 633, and an OFF button 634. Sine wave 632 selects a normal signal type (see signal 2110 in FIG. 21) while OFF button 633 selects alpha-signal (see signal 2120 in FIG. 21) and OFF button 634 selects beta-signal (see signal 2130 in FIG. 21). A Wi-fi button 631 indicates the wireless connection such as Wi-fi, Bluetooth, Z-wave, Zigbee, or near field RF communication.

A START button 621 starts generating the treatment signal at PHV button 431 or NHV button 432. This treatment voltage level selected by VLT button 611. The treatment time duration is selected by Time+ 612, Time− 613. The display time 615 automatically counts down by one unit every minute. WAVE button 625 selects regular type of treatment signal. When START button 621 is pressed with either OFF buttons 633-634, treatment signal type is selected.

When IF button 623 is pressed, 2,800 Vp at 70 KHz sine wave is selected; and when START button 621, IF signal is displayed at display 615.

A SMART button 623 is designed to select the smart pre-programmed or preselected therapy function. When pressing START button 621, the treatment signals will be emitted in the order as shown Table 1 at PHV output 432 or alternatively at NHV output 431.

TABLE 1

Output Voltage with Different Waveforms and Corresponding Treatment time in 90 Minutes (S: Sine, A: Alpha, B: Beta).

| PHV | S4500 | A9000 | B14000 | S14000 | A16000 | A4500 | B4500 | S9000 | A14000 | S16000 |
|---|---|---|---|---|---|---|---|---|---|---|
| Time (min) | 10 | 10 | 10 | 10 | 10 | 10 | 10 | 10 | 10 | 10 |

A Sleep button 625 is designed to select the night therapy function, when Sleep button 625 and then START button 622 are pressed, the treatment signals will be emitted in the order as Table 2 at PHV (NHV).

TABLE 2

Output Voltage with Different Waveforms and Corresponding Treatment Time in 60 Minutes (S: Sine).

| PHV (NHV) | S3000 | S1500 | S1000 | S800 |
|---|---|---|---|---|
| Time (min) | 10 | 30 | 10 | 10 |

Continuing with FIG. 6, HMI screen 401 communicates with an IoT microcontroller (IoT MCU-1) 641, a microcontroller (MCU 2) 642, and relays system (RS1) 643 via a communication link governed by a MODBUS protocol 651. MODBUS 651 is a client/server data communication protocol in the application layer of HS-16000 Vp device 400. In some embodiments of the present invention, IoT MCU-1 641 uses Wi-Fi communication 652 and connects to MCU-2 642 via Universal Asynchronous Receiver/Transmitter (UART) channel. MCU-2 642 receives analog to digital converter (ADC) signals from protector circuit 429. In turn, MCU-2 642 controls OSC circuit 403 and relays system 643 via either wired or wireless communication channels.

Now referring to FIG. 7, a schematic diagram of an AC input filter 700 (filter 700) in accordance to an exemplary embodiment of the invention is illustrated. filter 700 provides AC voltage for the 70 KHz oscillation circuit and DC power circuits. In some preferred embodiments, the components, values, and connections of filter 700 are shown in FIG. 7. The input terminals of filter 700 has an L input 701 and an N input 702. Usually, N input 702 is an electrical ground, and L input 701 is where signal to be filtered applied. The output terminal of filter 700 is an output L-filter terminal 707. In operation, filter 700 is an 70 kHz LC bandpass filter including C8 709, C9 706, C10 703, C11 704, C12 705, L2 708, L1 710 with respective values and connections as shown. In operation, filter 700 only passes 70 kHz signals from OSC circuit 403 and filters out other high frequency interferences from OSC circuit 403 itself and/or from surrounding signal sources. The high frequency or RF interferences may be radiated from microwave ovens, wireless phones, radar signals, Bluetooth, electromagnetic interference (EMI), radio cross talks, or the likes. These high frequency interferences adversely affect the operations of HS-16000 Vp device 400 and must be eliminated.

Figure 8:
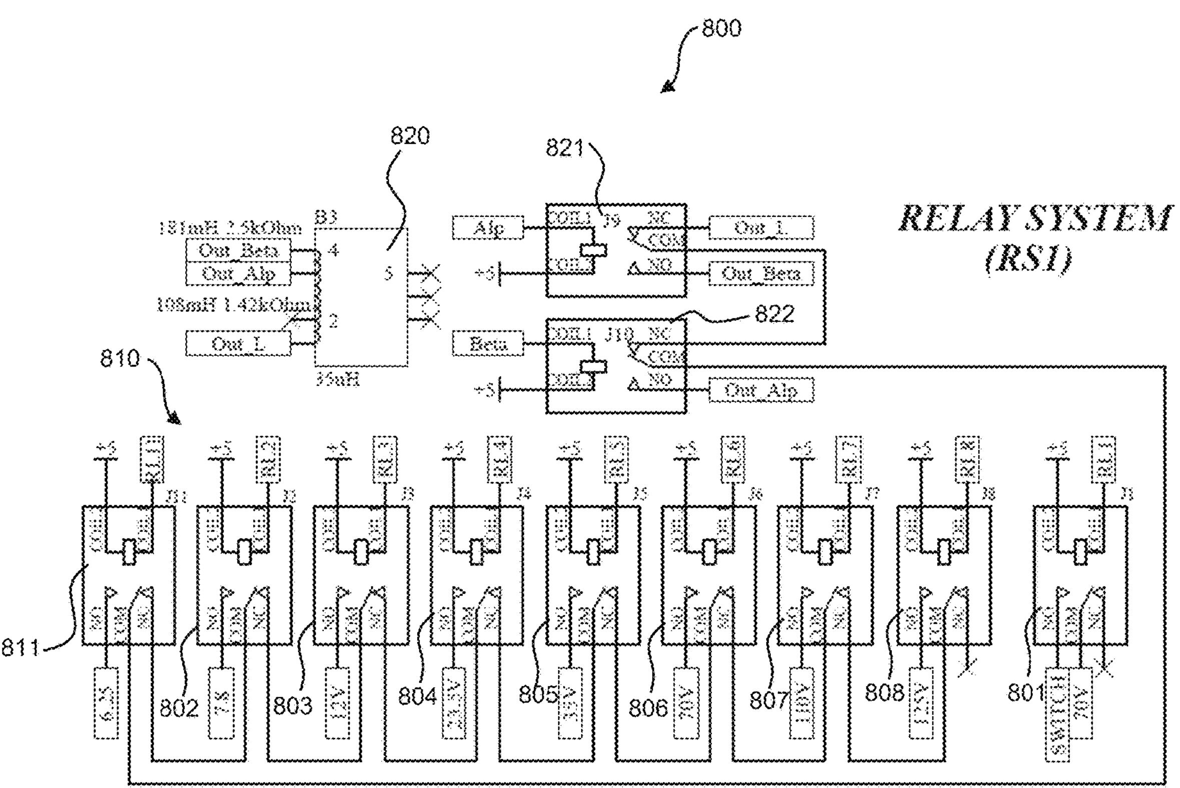
FIG. 8 shows a schematic diagram of the reset system (RS1) with alpha (Lα) and beta inductors (Lβ) that receive low voltages in accordance with an exemplary embodiment of the present invention.

Next in FIG. 8, a schematic diagram of the relay system (RS1) 800 in accordance to an exemplary embodiment of the present invention according to an exemplary embodiment of the invention is illustrated. RS system (RS1) 800 provides primary voltage sources to high voltage transformer circuit (HVT) 430. In other words, HVT 430 takes the low voltages from RS1 430 and transforms them to high voltages. These high voltages include standard sine (S-wave), Alpha sine (Out-Alp) and Beta sine (Out-Beta) signals. RS1 800 includes eleven relay circuits RL1 801-RL11 811 connected as shown in FIG. 8. A relay circuit is a switch that is controlled by magnetic fields generated by magnetic coils. Each of eleven relay circuits 801-811 includes a switch such as single pole double throw (SPDT) on the input terminal and a magnetic coil on the output terminal. The input terminal of each relay circuit includes an input node (NO), a common node (NC), and a communication (COM) node. The input node (NO) is connected to a low voltage source such as 6.25V, 7.8V, 12V, 23.5V, 35V, 70V, 110V, 125V. The low voltage sources are generated by low voltage transformer (LVT) circuit 422 which takes input from wall outlet source of 110V/220V at 50/60 Hz. The connections for RS1 800 is connected as follows. The NC node of RL11 811 is connected to COM node of RL2 802. The NC node of RL02 802 is connected to COM node of RL3 803. The NC node of RL03 803 is connected to COM node of RL4 804. The NC node of RL04 804 is connected to COM node of RL5 805. The NC node of RL05 805 is connected to COM node of RL6 806. The NC node of RL06 806 is connected to COM node of RL7 807. The NC node of RL07 807 is connected to COM node of RL8 808. The COM node of RL11 811 is connected to the COM node of a Beta inductor 821. The NC node of beta coil 822 is connected to the COM node of alpha coil 821. The NC node of alpha inductor 821 is connected to Out_L terminal, while the NO node of beta coil 822 is connected to Out_Alp. Alpha coil 821 is the same as first (alpha) inductor (Lα) 427 and beta coil 822 is the same as inductor (Lβ) 428. In many embodiments of the present invention, alpha inductor (Lα) 821 and beta inductor (Lβ) 822 each is a relay circuit with an input terminal and an output terminal. The input terminal includes a first coil connected to an alpha control signal (Alp) and a second coil connected to +5 Volts. The output terminal includes a COM node, a NO node, and an NC node. A schematic diagram 820 represents the combination of alpha inductor (Lα) 821 and beta inductor (Lβ) 822. The impedance of the first coil is 181 mH at 2.5 kΩ and that of the second coil is 108 1.42 kΩ.

Continuing with FIG. 8, the input node (NO) of RL1 circuit 801 is connected to 70V, the input node (NO) of RL2 circuit 802 is connected to 7.8V, the input node (NO) of RL3 circuit 803 is connected to 12V, the input node (NO) of RL4 804 is connected to 23.5V, the input node (NO) of RL5 circuit 805 is connected to 35V, the input node (NO) of RL6 circuit 806 is connected to 70V, the input node (NO) of RL7 circuit 807 is connected to 110V, the input node (NO) of RL8 circuit 808 is connected to 125V, and the input node (NO) of RL11 circuit 811 is connected to 6.25V signal source. In operation, RS circuit 800 is operative to select one to eight AC inputs that is fed into HVT high voltage transformer 430. The outputs of HVT 430 is high voltage therapy ranging from 800V to 16,000V. RL1 circuit 801 is a relay circuit that transforms 70 VAC using OSC circuit 403 that generates 2,800 Vp at 70 kHz at the IF output connector 406.

Figure 9:
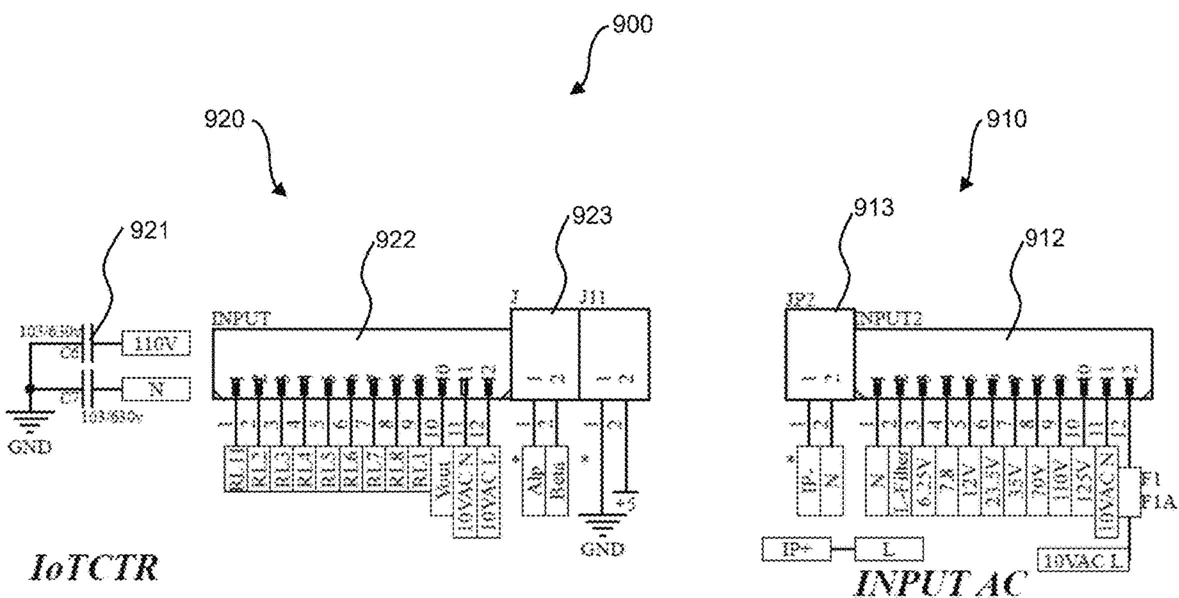
FIG. 9 shows a schematic diagram of a connector band in the IoT controller (IoTCTR) that supplies controlling signals to the connector band of the AC input voltages in accordance with an exemplary embodiment of the present invention.

Next referring to FIG. 9, a schematic diagram of input connector arrays 900 for two input sources including the IoT controller (IoTCTR) and the AC circuit in accordance with an exemplary embodiment of the present invention. Input connector arrays 900 include an IoTCTR input connector array 910 with a connector band 912 that is electrically connected to RS1 810 of FIG. 8. IoTCRT input connector array 910 is operated on an 110V power supply 911. A low input voltage AC connector band 920 includes a relay connector band 921 and a jumper 922 operative to provide low voltages to relay system (RS1) 800. In operation, IoTCRT input connector array 910 receives instructions from HS-16000 Vp device 400 (see FIG. 6). Low input voltage AC connector band 920 receives the low voltages from low voltage transformer (LVT) while connector band 812 transfers these instructions to RS1 800.

Figure 10:
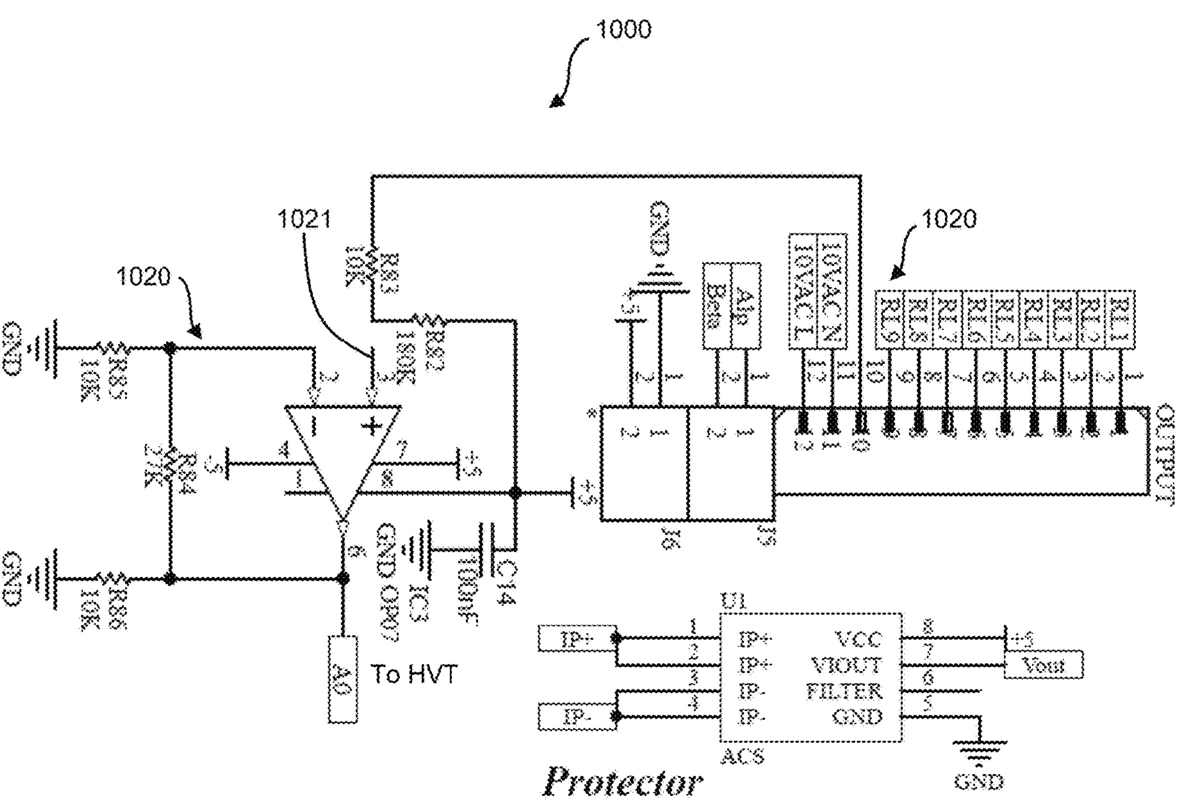
FIG. 10 shows a schematic diagram of the amplifier, the connector band, and a protector circuit in accordance to an exemplary embodiment of the invention.

Referring to FIG. 10, a schematic diagram of an output protector circuit 1000 in accordance with an exemplary embodiment of the present invention. Output protector circuit 1000 is an overcurrent protection circuit in front of the primary coil input of the high voltage transformer circuit (HVT) 430. Output protector circuit 1000 uses a current sensor to take the signal and amplify it before sending it to MCU1-IoTCTR 641 to control and protect the system when performing the therapy function. Protector circuit 1000 includes an output a current sensor IC 1010, an op-amp amplifier 1020, and an output connector band 1030. Current limiting IC 1010 is connected to limit the voltages at IP+ and IP− terminals of HVT circuit 1030. After that, the limited voltage is fed to op-amp amplifier 1020. The output of op-amp amplifier 1020 is input to IoTCTR 1030, to IoTCTR input band 900, and to HVT circuit 1030.

Figure 11:
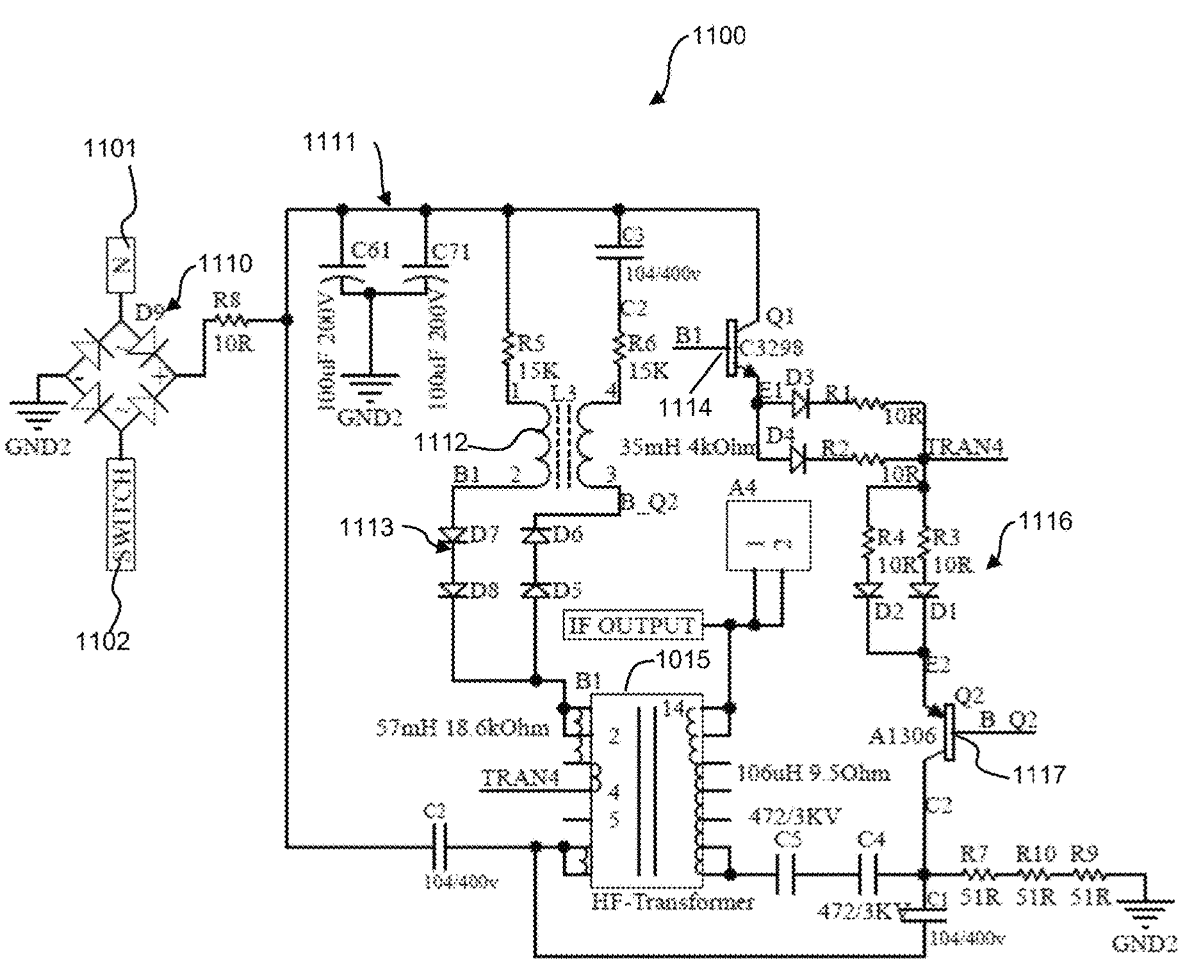
FIG. 11 shows a schematic diagram of an oscillator circuit (OSC) for generating 2,800 Vp at frequency 70 kHz in accordance with an exemplary embodiment of the present invention.

Referring to FIG. 11, a schematic diagram of a sinusoidal oscillator circuit 1100 in accordance with an exemplary embodiment of the present invention is illustrated. Oscillator circuit 1100 is an intermediate frequency (IF) sinusoidal oscillator circuit that outputs 2,800 Vp at a frequency of 70 KHz. At first, the 70V AC signal is received at terminals 1101-1102 and rectified by a full wave rectifier 1110. Then, an output signal at 2,800 Vp at 70 kHz is generated by the oscillator formed by capacitors 1111, an inductor 1112, diodes D5-D7 1113, npn BJT transistor Q1 1114, diodes D1-D4 1116, and a pnp BJT transistor Q2 1117. The 70 kHz oscillated signal is transformed to 2,800 Vp by an IF transformer 1115. The output amplitude of 2,800 Vp at 70 kHz provides IF therapeutic signal at IF output connector 406 (see FIG. 4). This IF output is useful for visceral fat reduction therapy function.

Figure 12:
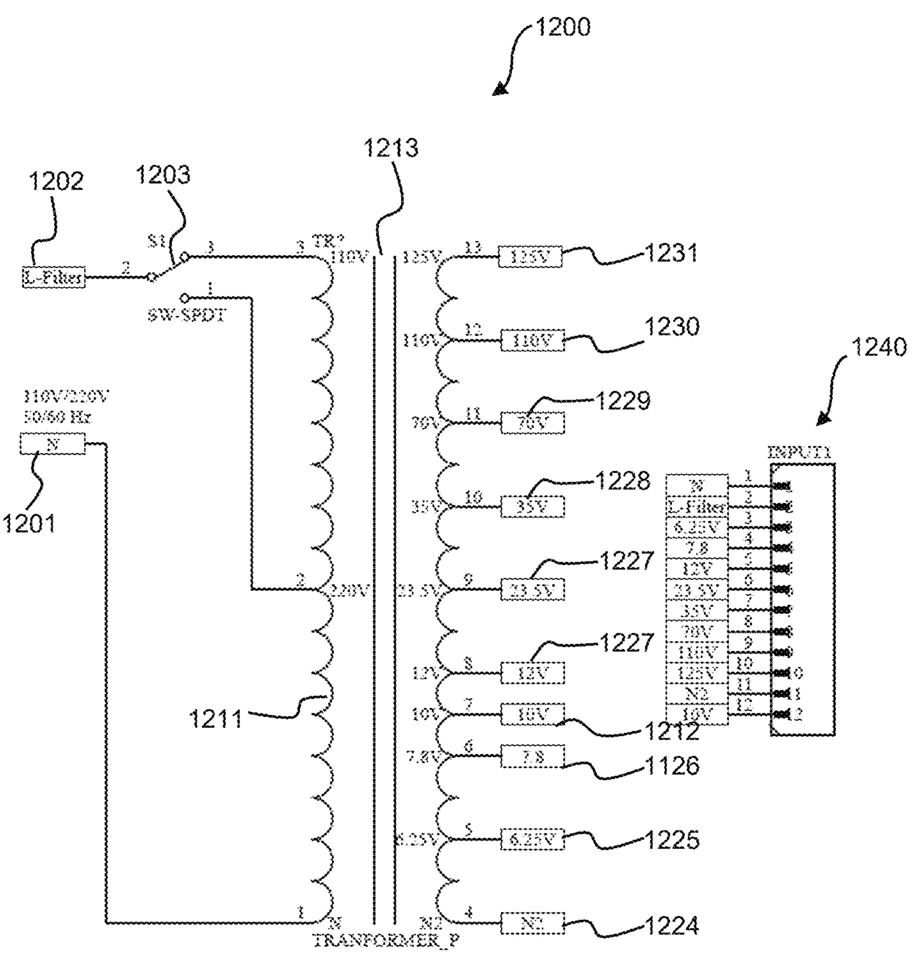
FIG. 12 shows a schematic diagram of a low voltage transformer (LVT) providing secondary voltages to the high voltage transformer (HVT) in accordance with an exemplary embodiment of the present invention.

Referring next to FIG. 12, a schematic diagram of a low voltage input transformer (LVT) 1200 for the HS-16000 Vp device in accordance with an exemplary embodiment of the present invention. In the present invention, the input can switch between 2 AC input voltage sources of 110V/220V at a frequency of 50 Hz/60 Hz and provide 8 primary output voltage sources to the high voltage transformer through the corresponding switching of the Relays during the therapy process. The eight primary output voltages sources include 6.25V source 1225, 10V source 1226, 18.5V source 1227, 37V source 1228, 74V source 1229, 110V 1230, and 125V source 1231. These eight primary voltage sources are applied to relay circuit RS1 via connector band 920 (see FIG. 9). Referring back to FIG. 4, AC output voltages 110V/220V at 50 Hz from wall outlet 421 is applied to input terminals 1201 and 1202. Low voltage transformer 1200 includes a single pole double throw (SPDT) switch 1203 that selects either 110V source or 220 V source. Then magnetic coil 1213 converts these AC signals (110V/220V) to eight different low voltage signals. These eight different low voltage signals are fed to AC input connector band 920.

Figure 13:
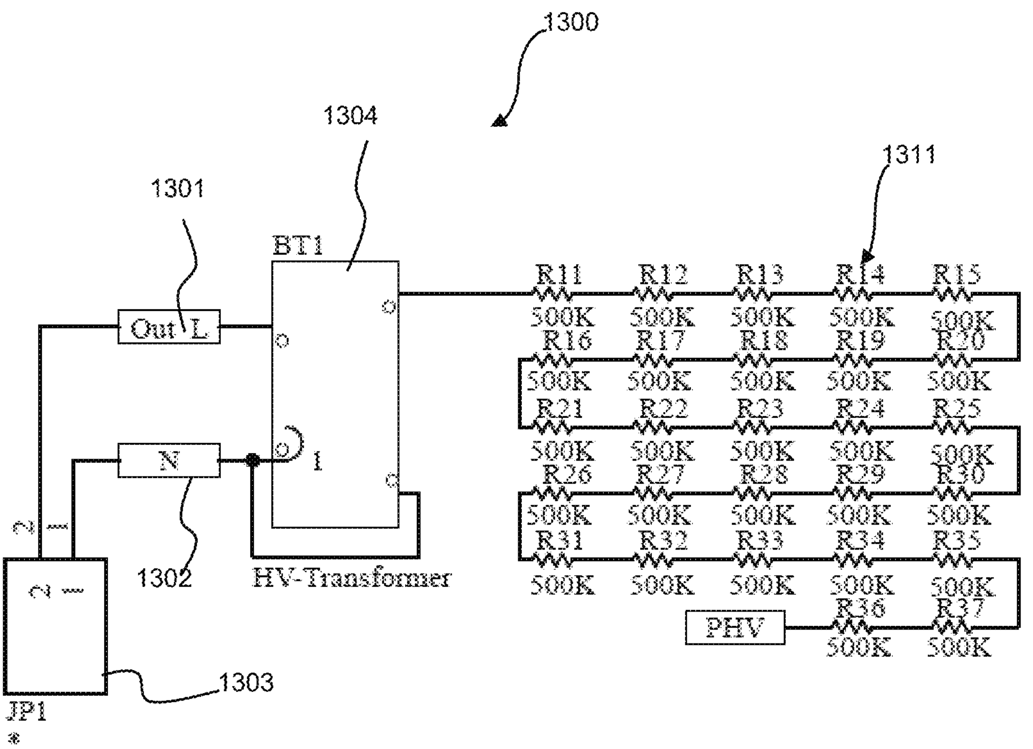
FIG. 13 shows a schematic diagram of a high voltage transformer (HVT) that generates positive high voltages (PHV) in accordance with an exemplary embodiment of the present invention.

Referring to FIG. 13, a schematic diagram of a high voltage transformer (HVT) circuit 1300 in accordance with an exemplary embodiment of the present invention is illustrated. High voltage transformer 1300 includes an interface device JP1 1301, an N terminal 1302, and Out_L terminal 1301, a high voltage transformer (HV) 1304. The input voltage at Out_L terminal 1301 is one of eight low voltages 1225-1231 (see FIG. 12) via filter 700. An N terminal 1302 is connected to N-terminal 702 of filter 700. Output of high voltage transformer 1304 is electrically connected to 3 W 500KΩ resistors connected in series and to PHV terminal. PHV terminal outputs 8,000V or 16,000V at PHV connector 431 or NHV connector 432. The 3 W 500 k resistors limit the output current to 5 mA.

Figure 14:
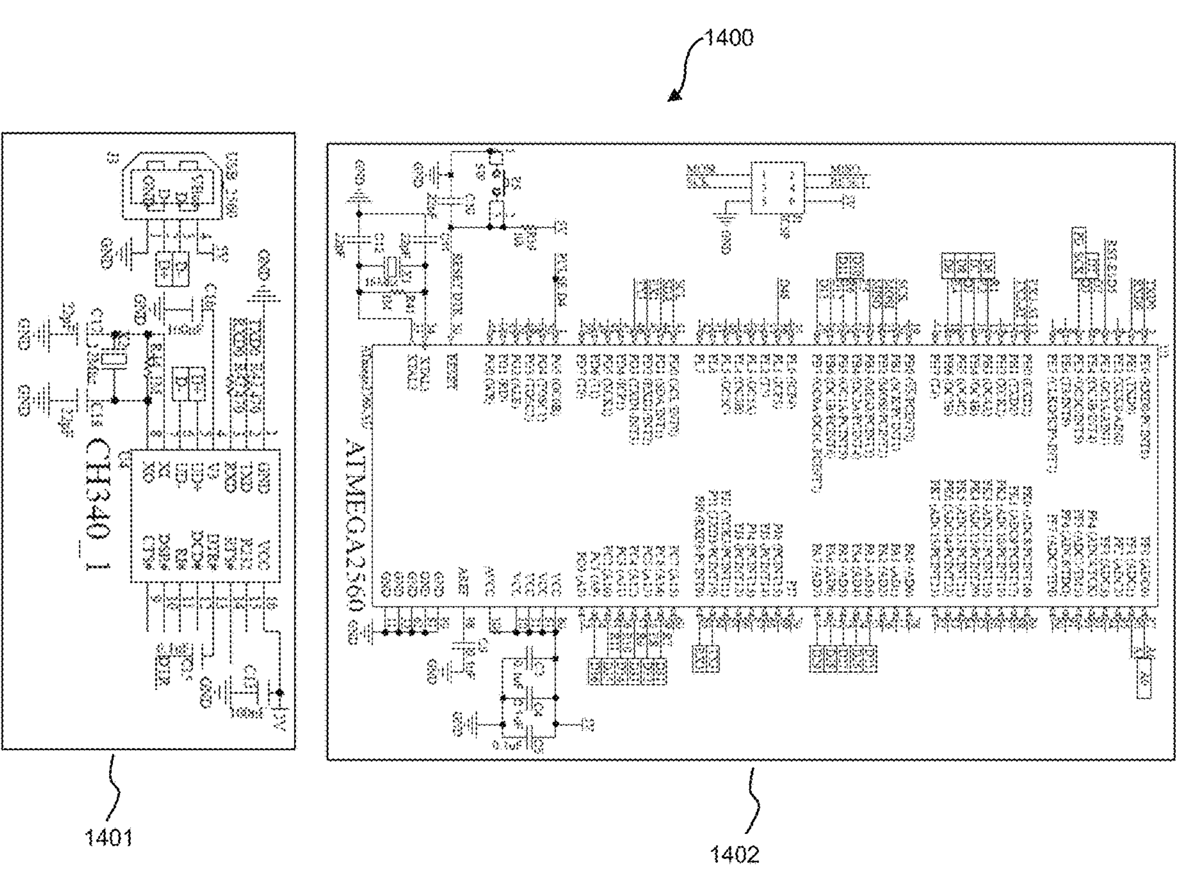
FIG. 14 shows a schematic diagram of a MCU1 that controls the operations of the high voltage HS-16000 Vp device in accordance with an exemplary embodiment of the present invention.

Referring to FIG. 14, a schematic diagram of a MCU1 circuit 1400 for controlling the operations of the high voltage HS-16000 Vp device in accordance with an exemplary embodiment of the present invention. MCU1 circuit 1400 uses a USB to serial IC 1401 to transfer the control operations from a computer to a microcontroller MCU 1402. MCU2 1402 is a low power CMOS microcontroller ATMEGA2560 that processes instructions for applications like sensor interfacing. MCU1 1400 receives instructions from USB IC 1401 and processes these instructions in serial data using universal asynchronous receiver transmitter (UART) protocol. More particularly, MCU1 1402 is a microprocessor that receives external instructions from USB circuit 1401 which is connected to external devices such as laptops, desktop computers, smart phones, tablets, or the likes. It is noted that in various embodiments of the present invention, USB IC 1401 is only an option for USB connections. External devices can communicate with MCU 1402 via wireless connections including Wi-fi, Bluetooth, Z-wave, Zigbee, near field communication (NFC), or other 802.11 wireless protocols.

Figure 15:
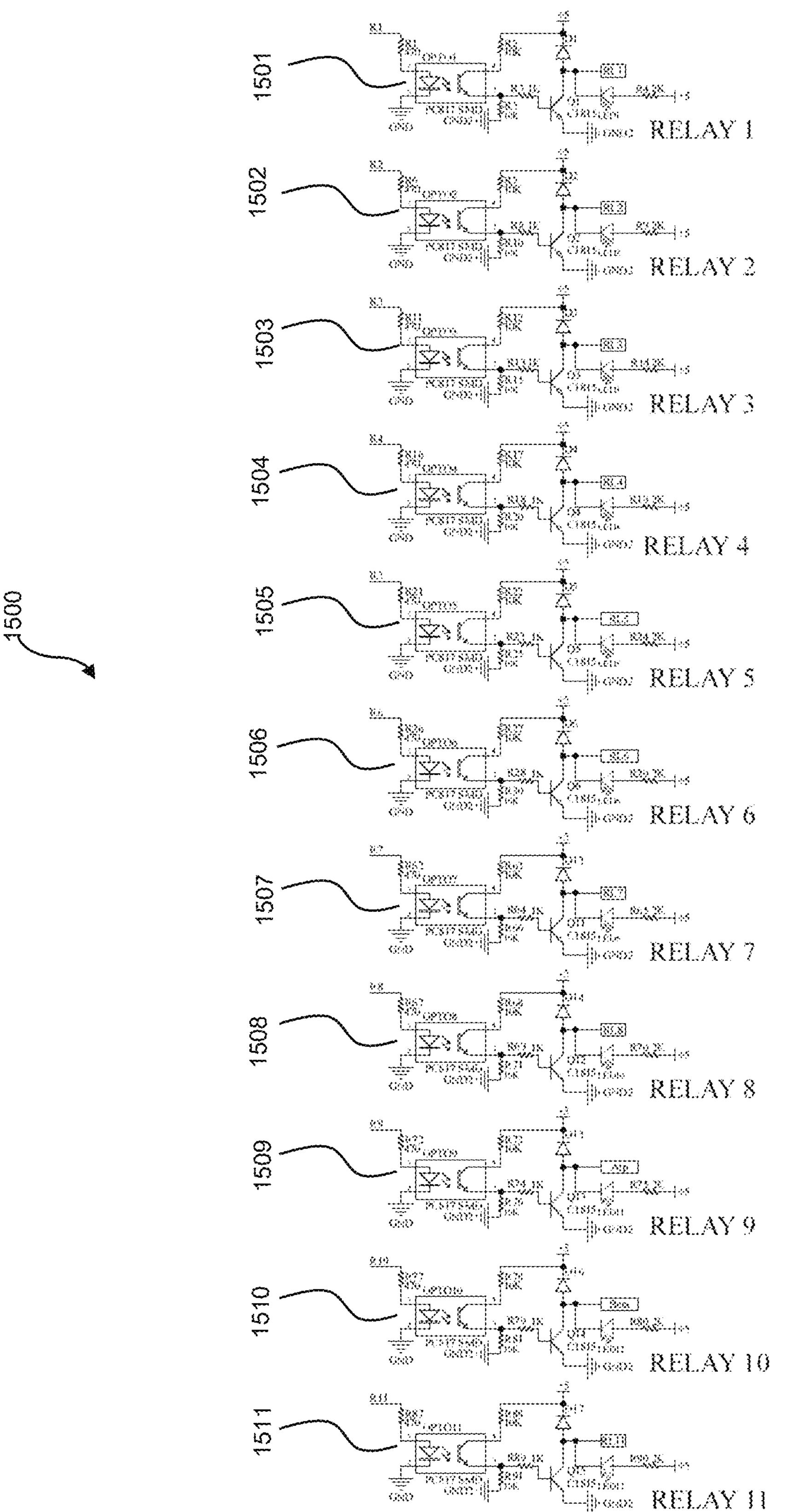
FIG. 15 shows a schematic diagram of a relay system for transferring low voltages to high voltages in accordance with an exemplary embodiment of the present invention.

Referring to FIG. 15, a schematic diagram of relay isolation circuit 1500 in accordance with an exemplary embodiment of the present invention is illustrated. Input photodiode circuit 1500 is designed to light up input signals that are selected. Input photodiode circuit 1500 transfers and turns on the corresponding photodiodes for signals from MCU1 1400 to RS1 circuit 500. Input photodiode circuit 1500 includes 11 relay circuits. They are a photodiode 1501, for relay 1, a photodiode 1502 for relay 2, a photodiode 1503 for relay 3, a photodiode 1504 for relay 4, a photodiode 1505 for relay 5, a photodiode 1506 for relay 6, a photodiode 1507 for relay 7, a photodiode 1508 for relay 8, a photodiode 1509 for relay 9, a photodiode 1510 for relay 10, and a photodiode 1511 for relay 11. Each photodiode circuit (1501 to 1511) includes transistors, diodes, and photodiodes connected as shown. An input signal, when selected, separately enter from the input resistor and output at the output transistor which causes the photodiode to light up.

Figure 16:
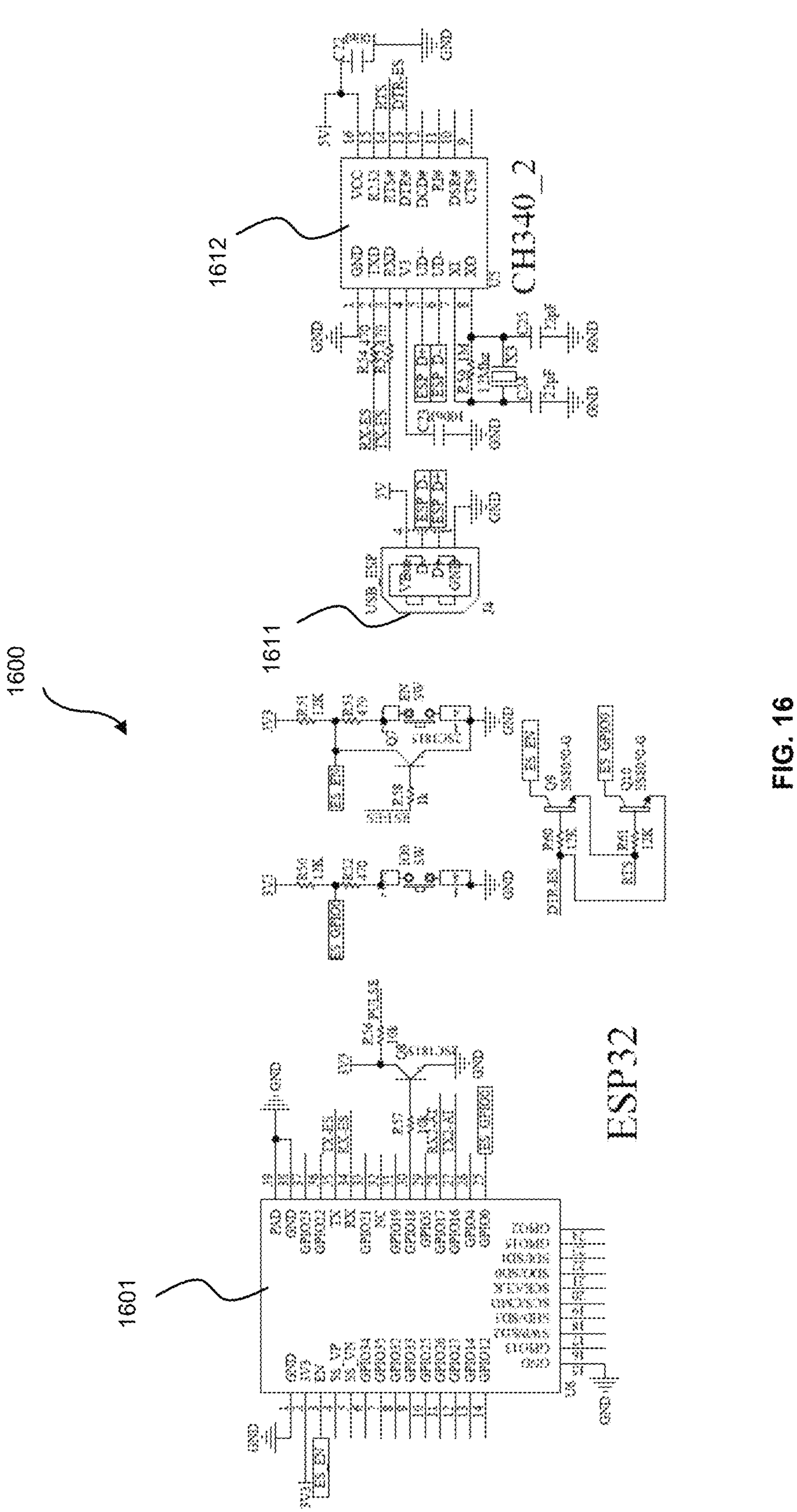
FIG. 16 shows an integrated circuit (IC) for IoTCTR MCU and an USB circuit in accordance with an exemplary embodiment of the present invention.

Referring next to FIG. 16, a schematic diagram of a MCU2 1600 for controlling the operations of the IoT devices in accordance with an exemplary embodiment of the present invention is illustrated. MCU2 circuit (IoT MCU) 1600 uses ESP32 microcontroller to allow communication to receive information to monitor the system's operation. MCU2 circuit 1600 also control the system's operations through MCU1 when necessary and send monitoring data to the Cloud via the Internet. MCU2 1600 includes an ESP32 is microcontroller system on chip (SoC) supporting 2.4 Ghz Wi-fi and BLUETOOTH® low energy (BLE) with 3.3V power supply 1602 and enable circuit 1603. An interface IC 1612 transfers the application program from a computer via a USB cable 1611 to a controller 1601 of the ESP32 system on chip (SoC) Controller 1611 processes APP mobile and Web applications using message query telemetry transport (MQTT) protocol.

Figure 17:
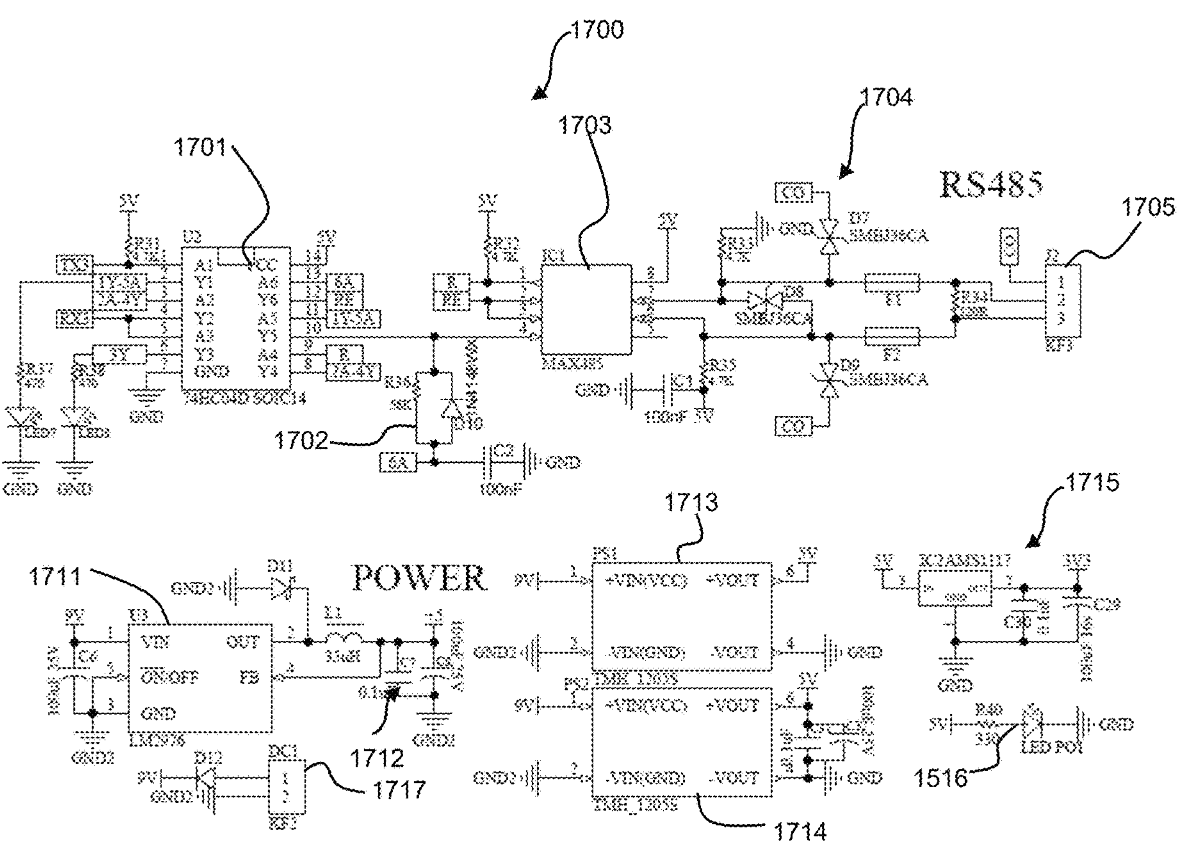
FIG. 17 shows a schematic diagram of an interface MODBUS circuit and USB circuit in accordance with an exemplary embodiment of the present invention.

Referring to FIG. 17, a schematic diagram of a DC supply voltage circuit and an interface MODBUS circuit 1700 in accordance with an exemplary embodiment of the present invention is illustrated. ICs 1701 to 1705 transfer to RS485 electrical serial communication. RS 485 is a twisted pair electrical cables for differential signals. IC 1711 to 1717 are power supply and DC to DC converters TMH1205 1713 and 1714 and buck converter SM2976 1711 operative to provide DC voltages to different units of HS-16000 Vp device 400.

Figure 18:
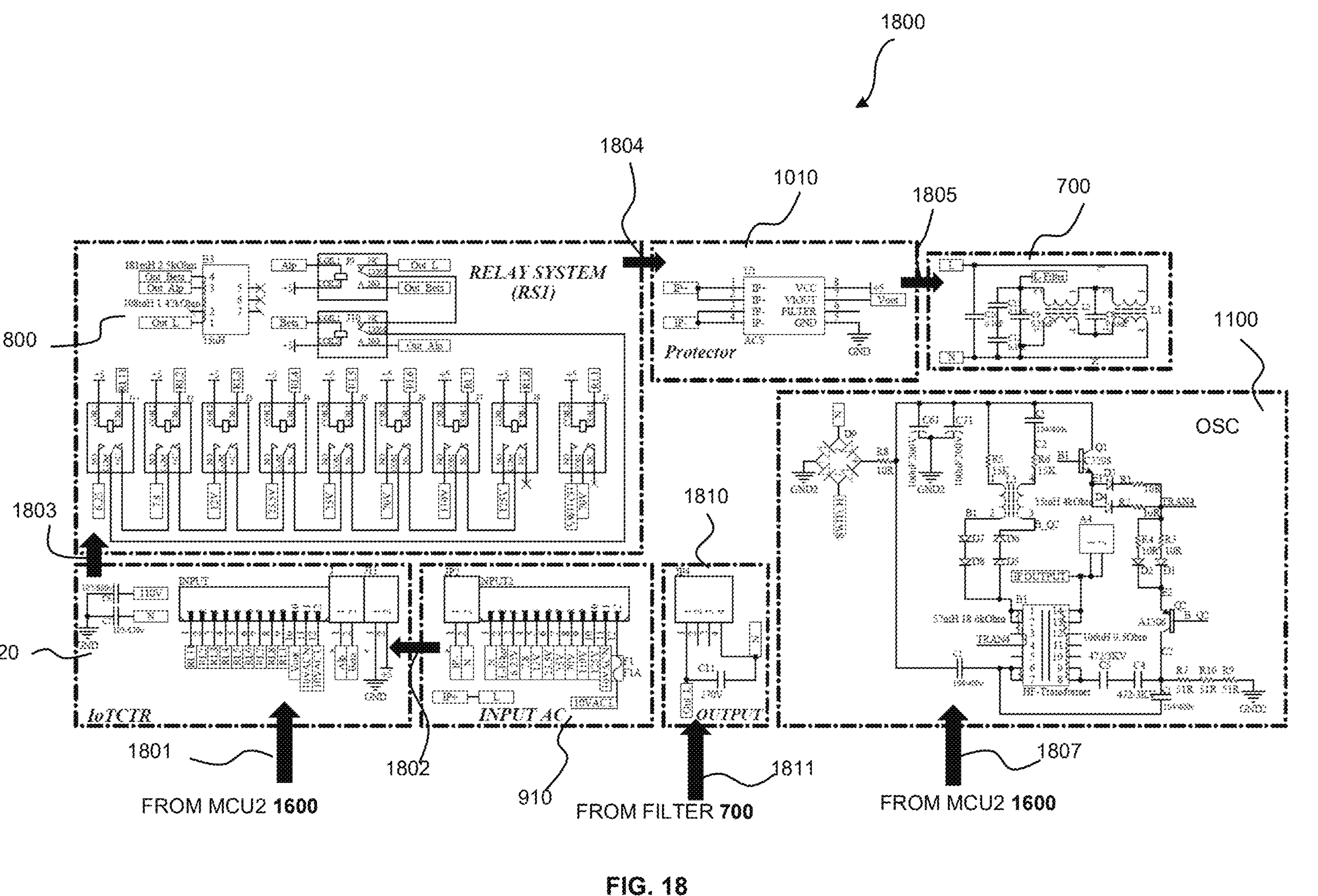
FIG. 18 shows a schematic of the components laid out on the first printed circuit board (PCB) of the HS-16000 Vp system in accordance with an exemplary embodiment of the present invention.

Referring to FIG. 18, a schematic diagram of components layout in first PCB 1800 of the HS-16000 Vp system in accordance with an exemplary embodiment of the present invention is illustrated. IoTCTR connector band 910 is a connector band to receive wireless signals from MCU2 1600 via a printed circuit board (PCB) traces 1801. Input AC connector band 910 receives 110V/220V 60 Hz AC signal from the wall outlets 421 and low voltages from LVT 1200. Input AC connector band 920 is connected to IoTCT connector band 910 via a PCB traces 1802. Relay system RS1 800 receives low input voltages relays from IoT connector band 910 via PCB traces 1803. RS1 800 switches these low voltage signals to HVT 430. The high voltages are fed to protector circuit 1010 via PCB traces 1804. Protector circuit 1010 eliminates electrical surges and overcurrents that may adversely affect HS-16000 Vp device 400. The protected output signal is fed to filter 700 via PCB traces 1805. Filter 700 filters out all internal cross-talks, electromagnetic interferences, as well as other unwanted signals. An output switch 1810 receives the filtered voltages via PCB traces 1811. Output switch 1810 sends out the final therapeutic voltages to PHV connector PHV 432. On the hand, if an IF voltage is selected, OSC 1100 receives instructions from MCU2 1600 via PCB traces 1807 to generate the IF therapy signal at 2,800 Vp at 70 kHz. IF signal is output at IF connector 406. Please note that PCB traces are thin, copper-conductive pathways on a printed circuit board (PCB) illustrated in FIG. 20.

Figure 19:
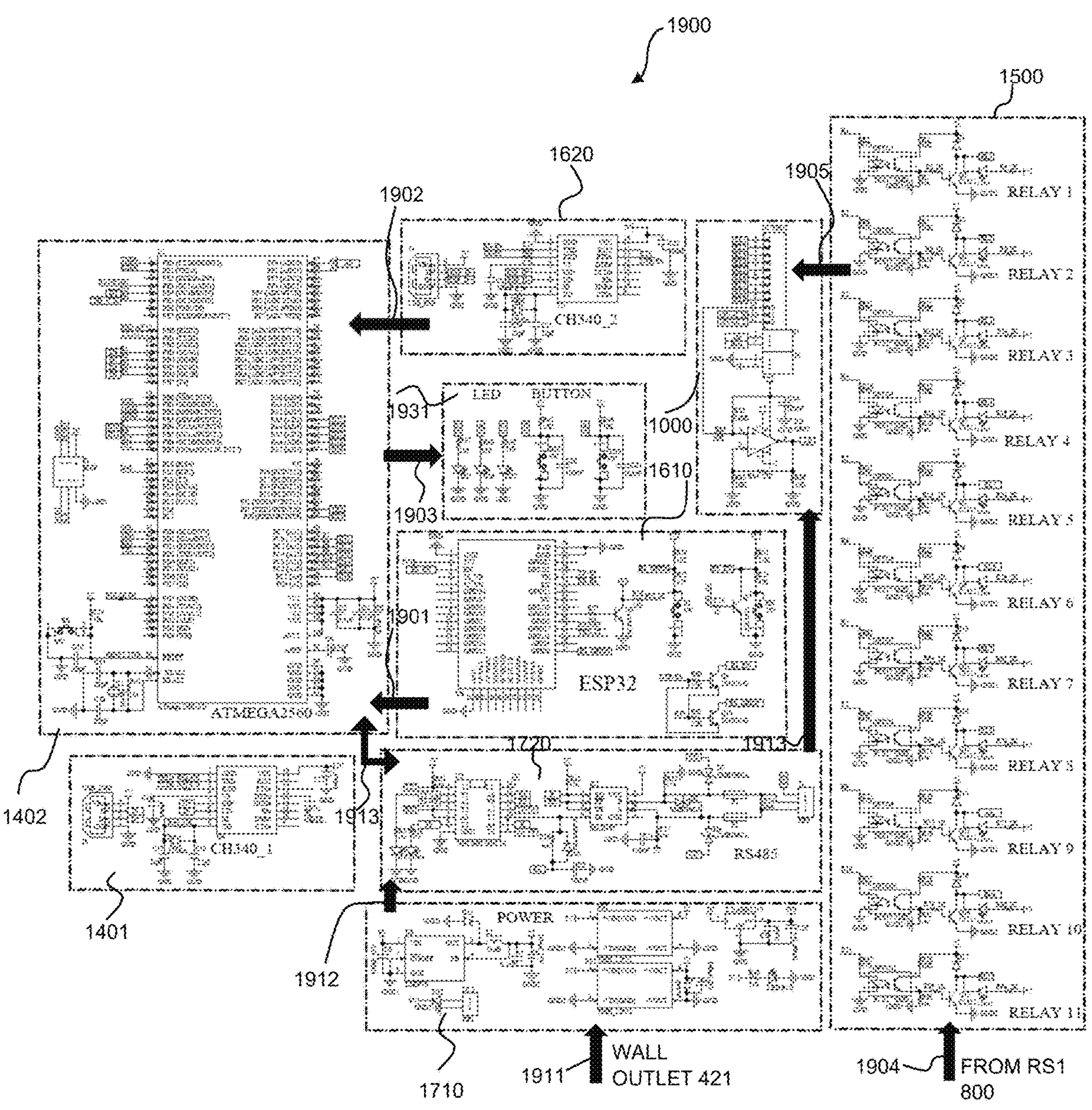
FIG. 19 shows a schematic of the components laid out on the second printed circuit board (PCB) of the HS-16000 Vp system in accordance with an exemplary embodiment of the present invention.

Referring to FIG. 19, a schematic diagram of components layout in a second PCB 1900 of the HS-16000 Vp system in accordance with an exemplary embodiment of the present invention is illustrated. First MCU1 1402 is microcontroller that receives instructions from second MCU electrical PCB traces 1902. AC input circuit 1710 receives 110V/220V 60 Hz AC signal from the wall outlets 421 via electrical connector 1911. PCB trace 1912 and input into regulator circuit 1720 for DC conversion and regulation. From there, voltage supplies are distributed to all components on second PCB via PCB traces 1913. Relay system RS1 1500 receives low input voltages relays from RS1 800 via PCB traces 1904. RS1 800 switches these low voltage signals to protector circuit 1000 before sending it to HVT 1300. The high voltages are fed to protector circuit 1010 via PCB traces 1804. Protector circuit 1000 eliminates electrical surges and overcurrents that may adversely affect HS-16000 Vp system 400. An LED circuit 1931 receives input signals from MCU1 1402 to alert users about the operating status of HS-16000 Vp 400.

Figure 20:
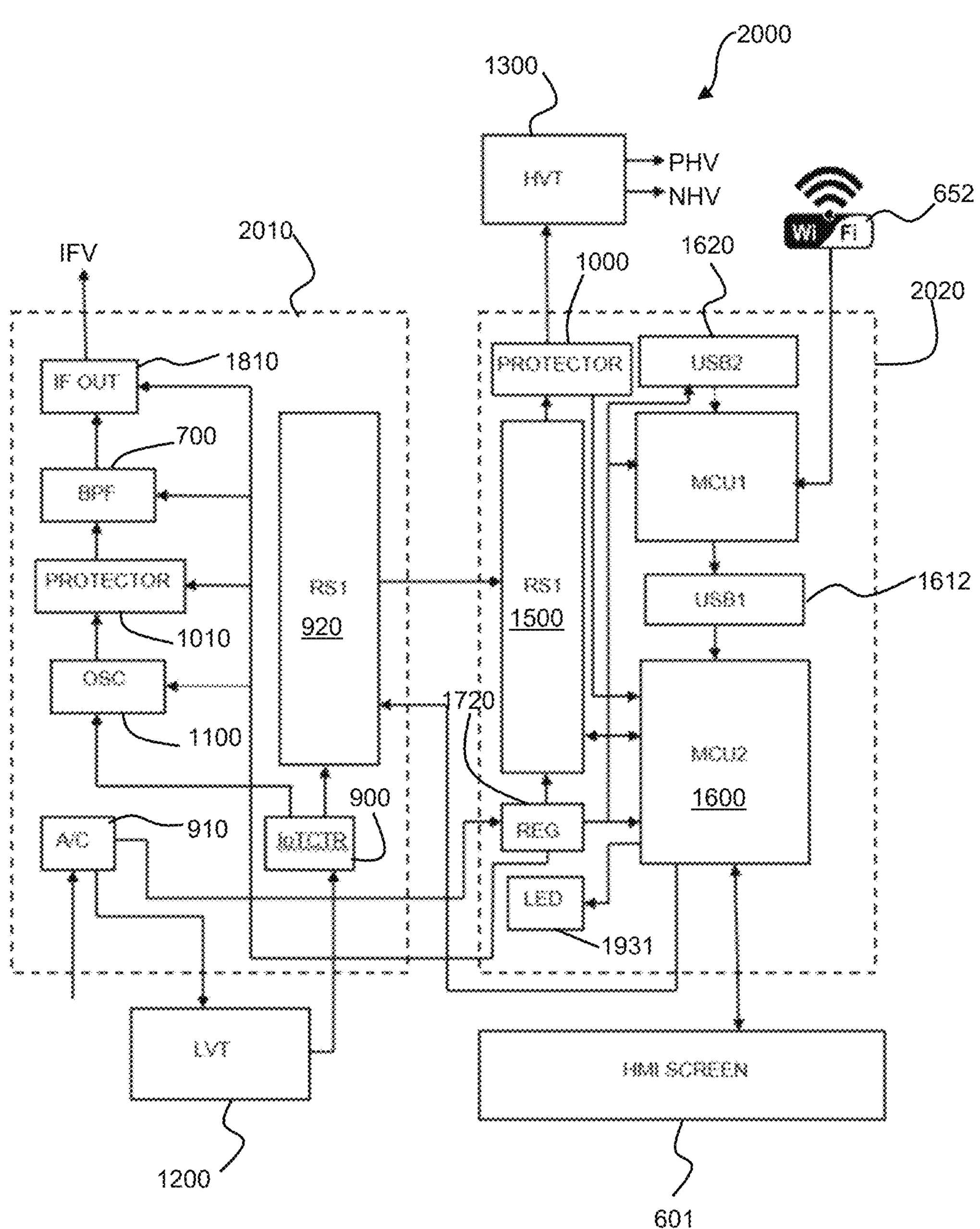
FIG. 20 shows the electrical connections and the schematic diagram of the first PCB and the second PCB the HS-16000 Vp system in accordance with an exemplary embodiment of the present invention.

Next, referring to FIG. 20, a schematic diagram 2000 of the entire HS-16000 Vp system on the first PCB and the second PCB in accordance with an exemplary embodiment of the present invention is illustrated. Low voltage transformer (LVT) 1200 and high voltage transformer (HVT) 1300 are connected to a first PCB 2010 containing the components listed and described in FIG. 18 and second PCB 2020 containing the components listed and described in FIG. 19. In some preferred embodiments of the present invention, HVT 1200 and HVT 1300 are laid outside of first PCB 2010 and second PCB 2020. The operation of HS-1600 Vp system 400 implemented by first PCB 2010 and second PCB 2020 are described in FIG. 4 and FIG. FIG. 24.

Figure 21:
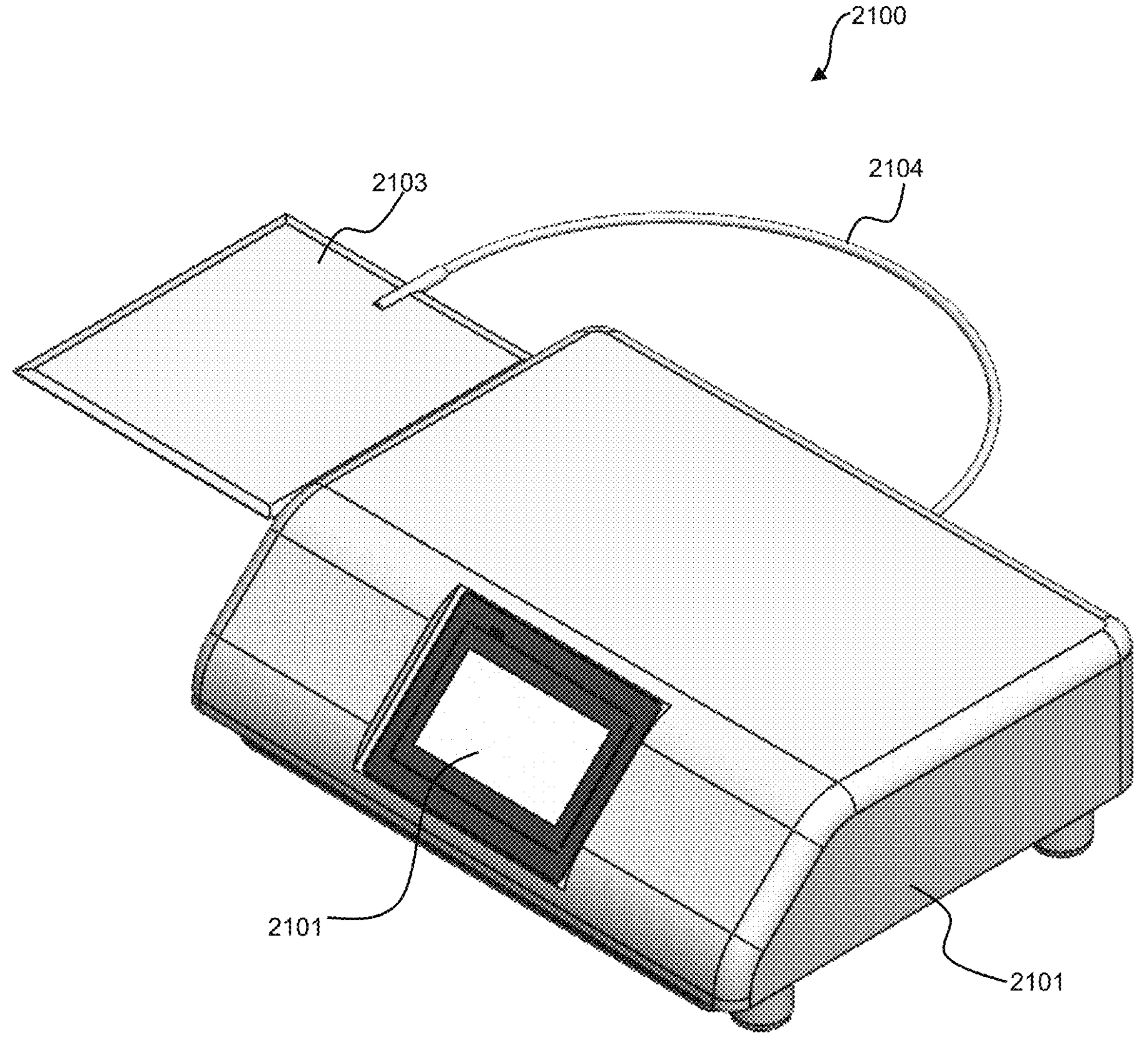
FIG. 21 shows 3D perspective diagram of the HS-16000VP system in accordance with an exemplary embodiment of the present invention.

In FIG. 21, a 3D perspective diagram of the HS-1600VP box 2100 in accordance with an exemplary embodiment of the present invention is presented. HS-1600 Vp system 2000 includes a PVC box 2101 and a human machine interface (HMI) 2102 for displaying the operational parameters of the therapeutic treatments. In some particular embodiments of the present invention, box 2100 has a trapozoidal prism with a width of 530 cm, a length of 427 cm and a height (depth) of 205 cm.

Figure 22:
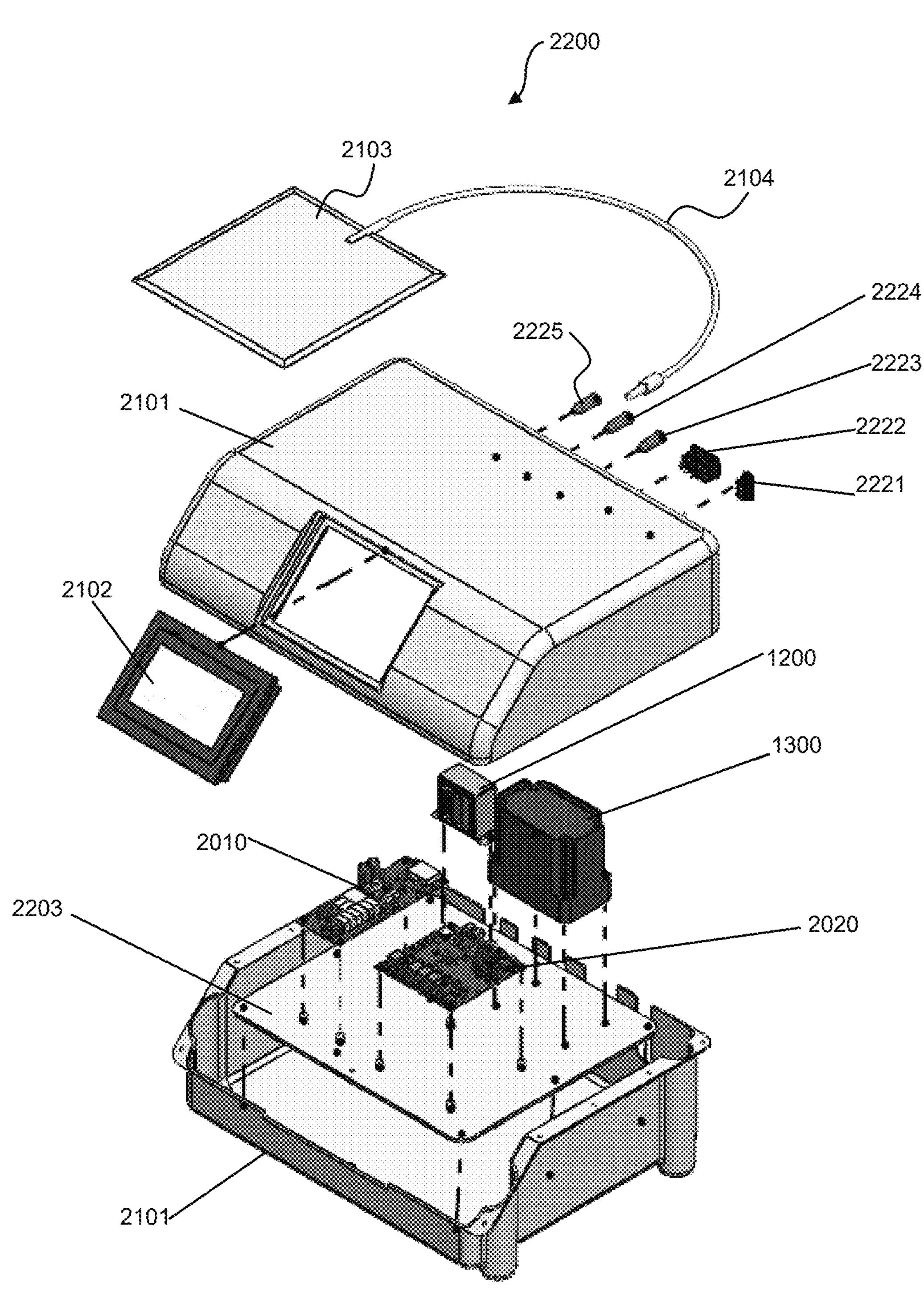
FIG. 22 shows 3D disassembled diagram of interior arrangement of the HS-16000 Vp system in accordance with an exemplary embodiment of the present invention in accordance with an exemplary embodiment of the present invention.

Next referring to FIG. 22, a 3D disassembly diagram 2200 of the HS-16000 Vp system in accordance with an exemplary embodiment of the present invention in accordance with an exemplary embodiment of the present invention is illustrated. Inside HS-16000 Vp box 2200 includes first PCB 2010, low voltage (LV) transformer 1202, high voltage (HV) transformer 1300, and main board 2203. In many embodiments of the present invention, in the back of HS-1600 Vp system includes a positive high voltage (PHV) connector 2225 for high voltage treatment regimes, a negative high voltage (NHV) connector 2224 for negative high voltage treatment regimes, and an IF connector 2223 is for IF voltage treatment regimes. An AC power input connector 2222 is for providing 110V/220V at 60 Hz voltage sources. A voltage switch 2221 is for selecting between 110V or 220V.

Figure 23:
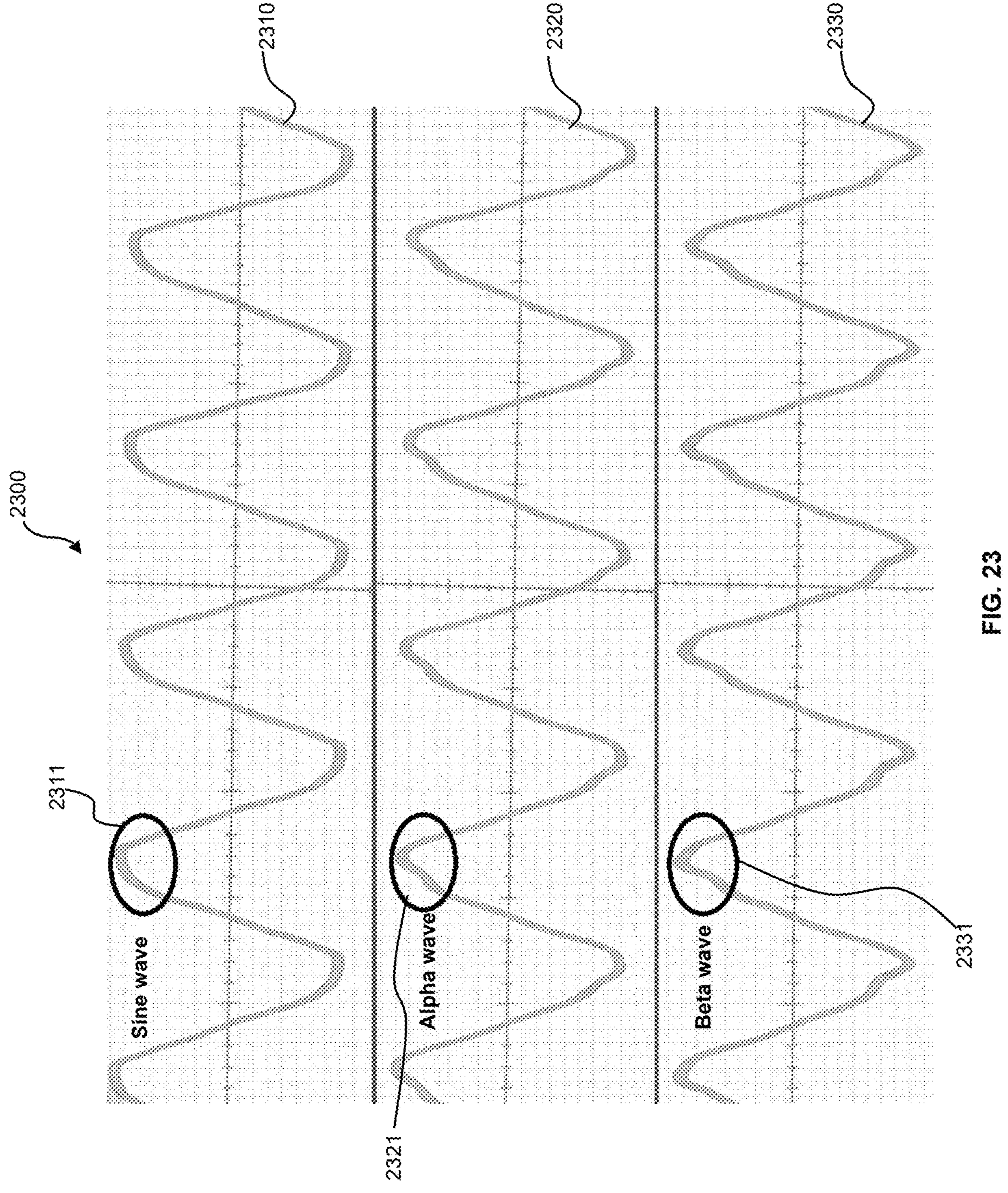
FIG. 23 shows the three different type of output signals in accordance with an exemplary embodiment of the present invention in accordance with an exemplary embodiment of the present invention.

Now referring to FIG. 23, different output treatment signals 2300 generated by HS-16000 Vp system in accordance with an exemplary embodiment of the present invention in accordance with an exemplary embodiment of the present invention are illustrated.

A sinusoidal signal 2310 is a basic therapy signal for high voltage treatments. Signal 2310 is used to smoothly regulate body functions and stabilize any biological variations, suitable for the first time patients, the elderly, and the people who do not have a strong physiological health. A signal 2320 is for a long term treatment. Signal distortion 2321 changes the derivatives of the applied voltages $$\frac{dV}{dt},$$

leading to differences in treatment phases.

Signal 2320 has an approximately 11.5 kV larger peak to peak compared to wave 2010. However, it can be used for sensitive patients with damaged tissues.

A signal 2330 has an approximately 8.75 kV larger peak to peak amplitude than signal 2310. This voltage difference gives signal 2330 a stronger differential power in a short time period, increasing epidermis penetration, fat tissues, and deep penetration to the hypodermis layer.

Signal distortions 2321 and 2331 incite faster ion transports across the plasma membranes of the cells, increasing cellular circulation and metabolism.

Figure 24:
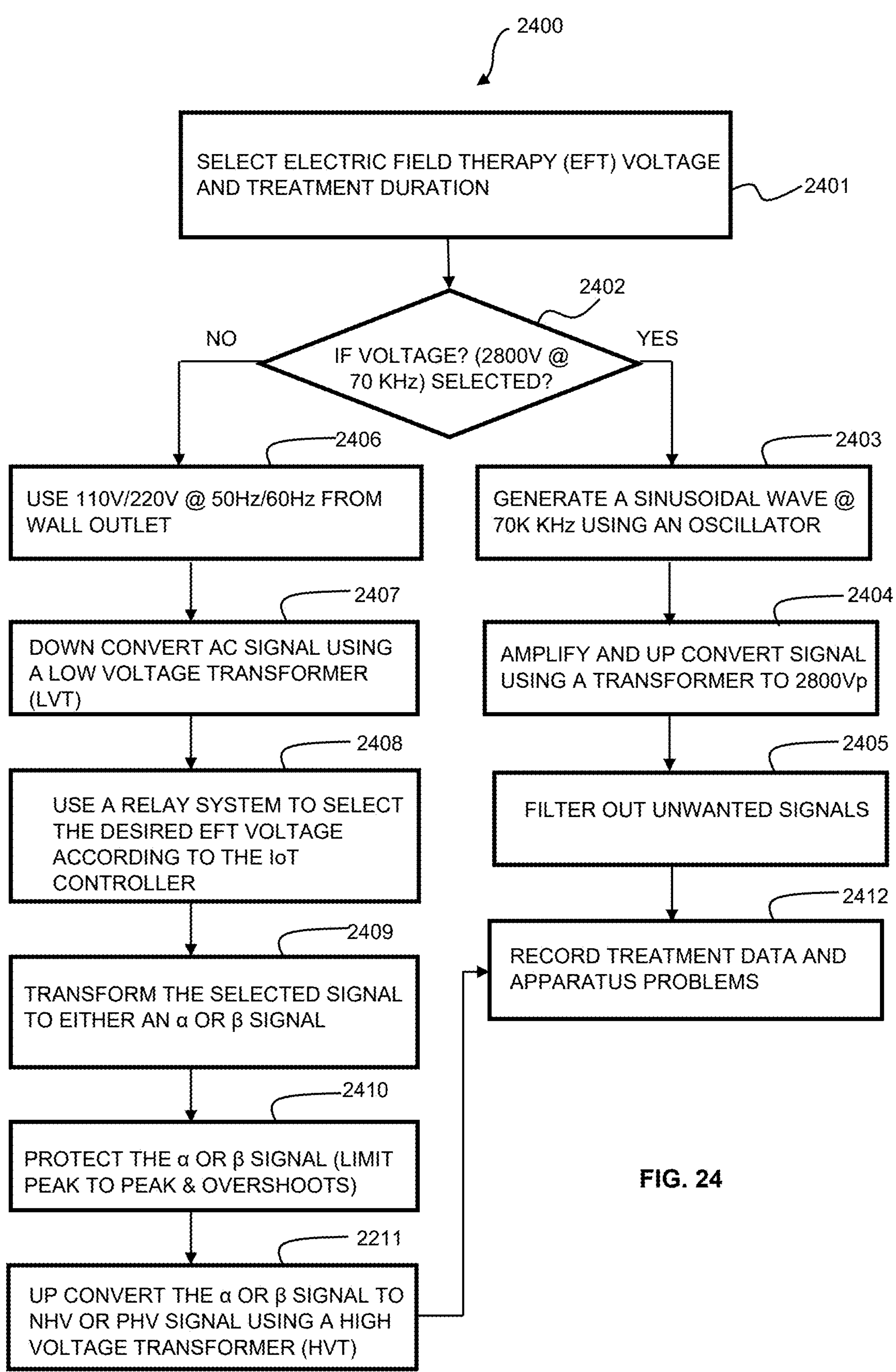
FIG. 24 shows a flow chart of an electroporation method for treating diseases in accordance with an exemplary aspect of the present invention.

Finally referring to FIG. 24, a flow chart of an electroporation method 2200 for generating an electric field therapy (EFT) voltage in accordance with an exemplary aspect of the present invention is illustrated. Method 2400 is implemented by HS-16000 Vp device 400 described above. Method 2400 generates different EFT voltages: an intermediate frequency (IF) voltage at 2800 Vp, 70 kHz; and various high frequency voltages selected from 800V, 1,000V, 1,500V, 3,000V, 4,500V, 9,000V, 14,000V, and 16,000V at 50 Hz/60 Hz available at either negative voltage (NHV) or positive high voltage (PHV) output 432.

At step 2401, a desired EFT voltage is chosen. Step 2401 is realized by HMI screen 401 or IoTCTR circuit 402. A user such as a doctor, a nurse, or a therapist uses HMI screen 401 in FIG. 6 to enter the EFT voltage and duration. VLT button 611 pressed for IF signal 406. Sine button 631 and OFF button 632 and 633 are selected for HELP (high voltage electric potential) ranging from 800 Vp to 16,000 Vp available at negative high voltage (NHV) 431 and positive high voltage (PHV) 432.

At step 2402, whether the chosen therapeutic voltage (EFT) is an intermediate frequency (IF) voltage with 2800 Vp voltage at 70 kHz. Similar to step 2401 above, step 2402 is realized by HMI screen 401 or remotely by IoTCTR circuit 402. In addition, MCU-2 642 can determine step 2402.

Next at step 2403, when the selected therapeutic voltage is an IF voltage (2800 Vp at 70 kHz), a sinusoidal voltage at 70 kHz is generated using an oscillator. In one aspect of the present invention, Step 2403 is realized by OSC circuit 1100.

At step 2404, the low voltage at IF frequency is filtered and amplified by class B amplifier and then up converted to achieved IF signal having a peak to peak amplitude of 2800 Vp at 70 kHz. Step 2404 is realized by high frequency transformer (HFT) 404.

At step 2405, the amplified signal is filtered to eliminate spurious and unwanted signals. Step 2405 is realized by IF filter 700.

At step 2406, when the selected therapeutic voltage is not an IF voltage, the AC wall outlet voltage at either 110V or 220V at 50 Hz/60 Hz is used as input voltage sources. Step 2406 is realized by HS-16000 Vp device 400 and wall voltage outlet sources 421.

At step 2407, the AC wall outlet voltage is down converted to different low voltage values. In the present invention, 8 low voltage values of 6.25V, 7.8V, 12V, 23.5V, 35V, 70V, 110V, and 125V are used. Step 2206 is realized by LVT transformer 422 and relay system RS1 510.

At step 2408, a desired voltage is selected. Step 2408 is realized by IoTCRT 402 and relay system RS1 510. In actuality, IoTCRT 402 sends a command signal selected by the user. The command signal switches on a particular relay (e.g., RL4 at 23.5V).

At step 2409, the selected low voltage signal is transformed to either an alpha-sine wave or beta-sine wave. Step 2409 is realized by the combination of RL9 423, RL10 424, RL11 425, inductor Lα 426, and inductor Lβ 427.

Next at step 2410, the alpha sine signal and the beta sine signal are protected. Step 2410 is realized by protector circuit 429. As described above protector circuit 429 prevents overshoots, electrical surges, and noises from corrupting the alpha sine signal and the beta sine signal.

At step 2411, the alpha sine signal and the beta sine signal are protected are up converted using a high voltage transformer. Step 2411 is realized by HVT transformer 430.

At step 2412, the treatment data and problems with HS-16000 Vp system are recorded. Step 2412 is realized by MCU1 (ATMEGA2560 1402).

In other aspects of the present invention, preprogrammed therapeutic stored in IoTCTR 402 as described in Table 1 and Table 2 can also be used to implement method 2200.

Although the implementation options of the present invention are disclosed through the detailed description of the invention above, however, it should be understood that the invention is by no means limited to these implementation options. Experts in the same technical field admit that many other similar changes and arrangements could be made. Therefore, the scope of the invention is clearly defined to include all similar changes and arrangements within the scope of the following attached claims.

REFERENCES

[1] V. Hubert, C. Dumot, E. Ong, C. Amaz, E. Canet-Soulas, F. Chauveau, M. Wiart, MRI coupled with clinically-applicable iron oxide nanoparticles reveals choroid plexus involvement in a murine model of neuroinflammation, Sci. Rep. 9 (1) (2019) 10046.

[2] H. Li, S. Yang, D. Hui, R. Hong, Progress in magnetic Fe3O4 nanomaterials in magnetic resonance imaging, Nanotechnol. Rev. 9 (1) (2020) 1265-1283.

[3] K. Wang, J. Wang, X. Xu, M. Rong, L. Lu, X. Zhao, Y. Wang, Y. Jiang, Fe3O4-rhodamine 6G nanoparticles: An iron enhanced pH sensitive multimodal probe for fluorescence and magnetic resonance imaging of tumor cell, J. Mater. Sci. Technol. 160 (2023) 128-138.

[4] J. Mistral, K. T. Ve Koon, L. Fernando Cotica, G. Sanguino Dias, I. Aparecido Santos, P. Alcouffe, N. Milhau, D. Pin, O. Chapet, A. Serghei, Chitosan-coated superparamagnetic Fe3O4 nanoparticles for magnetic resonance imaging, magnetic hyperthermia, and drug delivery, ACS Appl. Nano Mater. (2024).

[5] H. Yue, D. Zhao, T. Tegafaw, M. Y. Ahmad, A. K. A. A. Saidi, Y. Liu, H. Cha, B. W. Yang, K. S. Chae, S.-W. Nam, Core-shell Fe3O4@ C nanoparticles as highly effective T2 magnetic resonance imaging contrast agents. in vitro and in vivo studies, Nanomaterials 14 (2) (2024) 177.

[6] R. S. Das, D. Maiti, S. Kar, T. Bera, A. Mukherjee, P. C. Saha, A. Mondal, S. Guha, Design of Water-soluble rotaxane-capped superparamagnetic, ultrasmall Fe3O4 nanoparticles for targeted NIR fluorescence imaging in combination with magnetic resonance imaging, J. Am. Chem. Soc. 145 (37) (2023) 20451-20461.

[7] H. N. Pham, T. H. G. Pham, D. T. Nguyen, Q. T. Phan, T. T. H. Le, P. T. Ha, H. M. Do, T. M. N. Hoang, X. P.

Nguyen, Magnetic inductive heating of organs of mouse models treated by copolymer coated Fe3O4 nanoparticles, Adv. Nat. Sci. Nanosci. Nanotechnol. 8 (2) (2017) 025013.

[8] T. Sojkov´a, G. M. Rizzo, A. Di Girolamo, S. K. Avugadda, N. Soni, N. B. Milbrandt, Y. H. Tsai, I. Kubˇena, M. Sojka, N. Silvestri, From core-shell FeO/Fe3O4 to magnetite nanocubes: enhancing magnetic hyperthermia and imaging performance by thermal annealing, Chem. Mater. 35 (16) (2023) 6201-6219.

[9] M. Zuvin, E. Kuruoglu, V. O. Kaya, O. Unal, O. Kutlu, H. Yagci Acar, D. Gozuacik, A. Kos¸ar, Magnetofection of green fluorescent protein encoding DNA-bearing polyethyleneimine-coated superparamagnetic iron oxide nanoparticles to human breast cancer cells, ACS Omega 4 (7) (2019) 12366-12374. [

[10] C.-W. Lu, J.-K. Hsiao, H.-M. Liu, C.-H. Wu, Characterization of an iron oxide nanoparticle labelling and MRI-based protocol for inducing human mesenchymal stem cells into neural-like cells, Sci. Rep. 7 (1) (2017) 3587.

[11] Y. Wang, S. Ma, X. Liu, Y. Wei, H. Xu, Z. Liang, Y. Hu, X. Lian, D. Huang, Hyaluronic acid mediated Fe3O4 nanocubes reversing the EMT through targeted cancer stem cell, Colloids Surf. B Biointerfaces 222 (2023) 113071.

[12] R. P. Friedrich, I. Cicha, C. Alexiou, Iron oxide nanoparticles in regenerative medicine and tissue engineering, Nanomaterials (basel) 11 (9) (2021) 2337.

[13] Y. Luo, Y. Chen, Z. Gu, R. Ni, P. Feng, Z. Hu, L. Song, X. Shen, C. Gu, J. Li, Engineered muscle from microchanneled PEG scaffold with magnetic Fe3O4 fixation towards accelerating esophageal muscle repair, Materials Today Bio 23 (2023) 100853.

[14] H. R. Hosseini, M. Abdouss, M. Golshekan, Hydroxyapatite incorporated with Fe3O4@ MCM-41 core-shell: a promising nanocomposite for teriparatide delivery in bone tissue regeneration, ACS Omega 8 (44) (2023) 41363-41373. [

[15] S. Egodawatte, S. Dominguez Jr, S. C. Larsen, Solvent effects in the development of a drug delivery system for 5-fluorouracil using magnetic mesoporous silica nanoparticles, Micropor. Mesopor. Mater. 237 (2017) 108-116.

[16] W. Cai, W. Zhang, Z. Chen, Magnetic Fe3O4@ ZIF-8 nanoparticles as a drug release vehicle: pH-sensitive release of norfloxacin and its antibacterial activity, Colloids Surf. B Biointerfaces 223 (2023) 113170.

[17] M. Pourmadadi, M. Ahmadi, F. Yazdian, Synthesis of a novel pH-responsive Fe3O4/chitosan/agarose double nanoemulsion as a promising Nanocarrier with sustained release of curcumin to treat MCF-7 cell line, Int. J. Biol. Macromol. 235 (2023) 123786.

[18] H. V. T. Luong, M. T. Diep, N.Y. Nguyen, D. T. Pham, L. N. H. Cao, T. M. P. Ha, Alginate-functionalized Fe3O4 nanoparticles as a drug delivery system for targeted controlled release, J. Drug Delivery Sci. Technol. (2024) 105465.

[19] A. S. Thakor, S. S. Gambhir, Nanooncology: The future of cancer diagnosis and therapy, CA Cancer J. Clin. 63 (6) (2013) 395-418. [20]M. Zhou, X. Du, W. Li, X. Li, H. Huang, Q. Liao, B. Shi, X. Zhang, M. Zhang, One-pot synthesis of redox-triggered biodegradable hybrid nanocapsules with a disulfidebridged silsesquioxane framework for promising drug delivery, J. Mater. Chem. B 5 (23) (2017) 4455-4469.

[20] H. Mekaru, J. Lu, F. Tamanoi, Development of mesoporous silica-based nanoparticles with controlled release capability for cancer therapy, Adv. Drug Deliv. Rev. 95 (2015) 40-49.

[21] B. Ruhle, P. Saint-Cricq, J. I. Zink, Externally controlled nanomachines on mesoporous silica nanoparticles for biomedical applications, ChemPhysChem 17 (12) (2016) 1769-1779.

[22] E. A. Prasetyanto, A. Bertucci, D. Septiadi, R. Corradini, P. Castro-Hartmann, L. De Cola, Breakable hybrid organosilica nanocapsules for protein delivery, Angew. Chem. 128 (10) (2016) 3384-3388.

[23] L. Maggini, I. Cabrera, A. Ruiz-Carretero, E. A. Prasetyanto, E. Robinet, L. De Cola, Breakable mesoporous silica nanoparticles for targeted drug delivery, Nanoscale 8 (13) (2016) 7240-7247.

[24] J. G. Croissant, Y. Fatieiev, K. Julfakyan, J. Lu, A. H. Emwas, D. H. Anjum, H. Omar, F. Tamanoi, J. I. Zink, N. M. Khashab, Biodegradable oxamide-phenylene-based mesoporous organosilica nanoparticles with unprecedented drug payloads for delivery in cells, Chem.—European J. 22 (42) (2016) 14806-14811.

[25] J. Croissant, X. Catto"en, M. W. C. Man, A. Gallud, L. Raehm, P. Trens, M. Maynadier, J.-O. Durand, Biodegradable ethylene-bis (propyl) disulfide-based periodic mesoporous organosilica nanorods and nanospheres for efficient in-vitro drug delivery, Adv. Mater 26 (35) (2014) 6174-6180.

[26] Y. Chen, Q. Meng, M. Wu, S. Wang, P. Xu, H. Chen, Y. Li, L. Zhang, L. Wang, J. Shi, Hollow mesoporous organosilica nanoparticles: a generic intelligent framework hybridization approach for biomedicine, J. Am. Chem. Soc. 136 (46) (2014) 16326-16334

[28] S. Chinnathambi, F. Tamanoi, Recent development to explore the use of biodegradable periodic mesoporous organosilica (BPMO) nanomaterials for cancer therapy, Pharmaceutics 12 (9) (2020) 890.

[29]N. X. D. Mai, Y. T. Dang, H. K. T. Ta, J.-S. Bae, S. Park, B. T. Phan, F. Tamanoi, T. L. H. Doan, Reducing particle size of biodegradable nanomaterial for efficient curcumin loading, J. Mater. Sci. 56 (5) (2021) 3713-3722.

[30] A. Eftekhari, M. Dalili, Z. Karimi, S. Rouhani, A. Hasanzadeh, S. Rostamnia, S. Khaksar, A. O. Idris, H. Karimi-Maleh, M. L. Yola, Sensitive and selective electrochemical detection of bisphenol A based on SBA-15 like Cu-PMO modified glassy carbon electrode, Food Chem. 358 (2021) 129763.

[31] A. Hasanzadeh, B. Gholipour, S. Rostamnia, A. Eftekhari, A. Tanomand, S. Khaksar, R. Khalilov, Biosynthesis of AgNPs onto the urea-based periodic mesoporous organosilica (AgxNPs/Ur-PMO) for antibacterial and cell viability assay, J. Colloid Interface Sci. 585 (2021) 676-683.

[32] E. Doustkhah, H. Mohtasham, M. Hasani, Y. Ide, S. Rostamnia, N. Tsunoji, M. H. N. Assadi, Merging periodic mesoporous organosilica (PMO) with mesoporous aluminosilica (Al/Si-PMO): A catalyst for green oxidation, Mol. Catal. 482 (2020) 110676. [33]N. X. D. Mai, A. Birault, K. Matsumoto, H. K. T. Ta, S. G. Intasa-ard, K. Morrison, P. B. Thang, T. L. H. Doan, F. Tamanoi, Biodegradable periodic mesoporous organosilica (BPMO) loaded with daunorubicin: a promising nanoparticle-based anticancer drug, ChemMedChem 15 (7) (2020) 593-599.

[34] N. X. D. Mai, T.-H.-T. Nguyen, L. B. Vong, M.-H.-D. Dang, T. T. T. Nguyen, L. H. T. Nguyen, H. K. T. Ta, T.-H. Nguyen, T. B. Phan, T. L. H. Doan, Tailoring chemical compositions of biodegradable mesoporous organosilica nanoparticles for controlled slow release of chemotherapeutic drug, Mater. Sci. Eng. C 127 (2021) 112232.

[35] N. X. D. Mai, T.-H.-T. Nguyen, L. H. T. Nguyen, H. T. Nguyen, T. B. Phan, F. Tamanoi, L. B. Vong, T. L. H. Doan, Engineering biodegradable periodic mesoporous functionalized-organosilica nanocarriers for efficient paclitaxel delivery, Colloids Surf. A Physicochem. Eng. Asp. 656 (2023) 130405.

[36] N. X. D. Mai, H. D. Le, H. V. N. Tran, T. T. N. Tran, T. T. M. Le, N. H. T. Thi, L. T. Huynh, L. H. T. Nguyen, H. K. T. Ta, T. L. H. Doan, Engineering surface modification of biodegradable periodic mesoporous organosilica for adenosine loading, J. Porous Mater. (2024) 1-9.

[37] S. Kargar, D. Elhamifar, A. Zarnegaryan, Core-shell structured Fe3O4@ SiO2-supported IL/[Mo6019]: A novel and magnetically recoverable nanocatalyst for the preparation of biologically active dihydropyrimidinones, J. Phys. Chem. Solid 146 (2020) 109601.

[38] F. Taheri, D. Elhamifar, S. Kargar, A. Zarnegaryan, Magnetic silica supported propylamine/H3PW12040: A powerful and highly stable nanocatalyst for synthesis of tetrahydrobenzopyrans, Mater. Chem. Phys. 297 (2023) 127443.

[39] R. Mirbagheri, D. Elhamifar, M. Shaker, Yolk-shell structured magnetic mesoporous silica: A novel and highly efficient adsorbent for removal of methylene blue, Sci. Rep. 11 (1) (2021) 23259

[40] B. Abdollahi, D. Salari, M. Zarei, Synthesis and characterization of magnetic Fe3O4@ SiO2-MIL-53 (Fe) metal-organic framework and its application for efficient removal of arsenate from surface and groundwater, J. Environ. Chem. Eng. 10 (2) (2022) 107144.

[41] A. Cimen, A. Bilgic, M. Bayrak, Fabrication and characterization of new Fe3O4@ SiO2@ TiO2-CPTS-HBAP (FST-CH) nanoparticles for photocatalytic degradation and adsorption removal of rhodamine B dye in the aquatic environment, Heliyon 10 (7) (2024).

[42] M. Neysi, D. Elhamifar, Pd-containing magnetic periodic mesoporous organosilica nanocomposite as an efficient and highly recoverable catalyst, Sci. Rep. 12 (1) (2022) 7970.

[43] F. Mousavi, D. Elhamifar, S. Kargar, Copper/IL-containing magnetic nanoporous MCM-41: A powerful and highly stable nanocatalyst, Surf. Interfaces 25 (2021) 101225. [44]B. H. McDonagh, G. Singh, S. Hak, S. Bandyopadhyay, I. L. Augestad, D. Peddis, I. Sandvig, A. Sandvig, W. R. Glomm, L-DOPA-coated manganese oxide nanoparticles as dual MRI contrast agents and drug-delivery vehicles, Small 12 (3) (2016) 301-306.

[45] C. Tudisco, M. Cambria, F. Sinatra, F. Bertani, A. Alba, A. Giuffrida, S. Saccone, E. Fantechi, C. Innocenti, C. Sangregorio, Multifunctional magnetic nanoparticles for enhanced intracellular drug transport, J. Mater. Chem. B 3 (20) (2015) 4134-4145.

[46] E. Fantechi, C. Innocenti, M. Zanardelli, M. Fittipaldi, E. Falvo, M. Carbo, V. Shullani, L. Di Cesare Mannelli, C. Ghelardini, A. M. Ferretti, A smart platform for hyperthermia application in cancer treatment: cobalt-doped ferrite nanoparticles mineralized in human ferritin cages, ACS Nano 8 (5) (2014) 4705-4719.

[47] M. S. Amini-Fazl, R. Mohammadi, K. Kheiri, 5-Fluorouracil loaded chitosan/polyacrylic acid/Fe3O4 magnetic nanocomposite hydrogel as a potential anticancer drug delivery system, Int. J. Biol. Macromol. 132 (2019) 506-513.

[48]W. Cai, M. Guo, X. Weng, W. Zhang, G. Owens, Z. Chen, Modified green synthesis of Fe3O4@ SiO2 nanoparticles for pH responsive drug release, Mater. Sci. Eng. C 112 (2020) 110900.

[49] Z. Anfar, H. Ait Ahsaine, M. Zbair, A. Amedlous, A. Ait El Fakir, A. Jada, N. El Alem, Recent trends on numerical investigations of response surface methodology for pollutants adsorption onto activated carbon materials: a review, Crit. Rev. Environ. Sci. Technol. 50 (10) (2020) 1043-1084.

[50] X. Catto¨en, S. Kodjikian, P. Trens, Periodic mesoporous organosilica nanoparticles: Morphology control and sorption properties, Colloids Surf. A Physicochem. Eng. Asp. 677 (2023) 132325.

[51] J. Reinholz, C. Diesler, S. Schottler, ¨ M. Kokkinopoulou, S. Ritz, K. Landfester, V. Mail¨ander, Protein machineries defining pathways of nanocarrier exocytosis and transcytosis, Acta Biomater. 71 (2018) 432-443.

[52] M. Mousa, Y.-H. Kim, N. D. Evans, R. O. Oreffo, J. I. Dawson, Tracking cellular uptake, intracellular trafficking and fate of nanoclay particles in human bone marrow stromal cells, Nanoscale 15 (45) (2023) 18457-18472.

ABBREVIATIONS

ACTH: adrenocorticotropic hormone;
α-MSH: alpha-melanocyte-stimulating hormone;
CRH: corticotropin-releasing hormone;
DGLA: dihomo gamma-linolenic acid;
DHA: cis-4,7,10,13,16,19-docosahexaenoic acid;
EF: electric field;
EIA: enzyme immunoassay;
ELISA: enzyme-linked immunosorbent assay;
EMF: electromagnetic fields;
GLP-1: glucagon-like peptide 1;
GPR: G protein-coupled receptor;
GW1100:1-(4-ethoxycarbonylphenyl)-2-(4-fluorobenzylthio)-5-(2-ethoxy-5-pyrimidinylmethyl)-4-pyrimidinone;
HELP: high-voltage electric potential
IF: intermediate frequency
IL: interleukin; IFN: interferon; NK: natural killer
IoRCTR: internet of thing controller
MCU: microcontroller unit
OEA: oleoylethanolamide; POMC: proopiomelanocortin
OSC: oscillator
SRM: Selected Response Monitoring
TRPV1: transient receptor potential vanilloid-1
VLT: voltage
Vp: Voltage peak-to-peak or rail to rail.

EXPLANATION OF REFERENCE NUMERALS

400 schematic diagram of HS-16000 Vp system
401 HMI (human machine interface) screen
402 IoTCTR (MCU1)
403 IF oscillator (OSC)
404 IF transformer (IFT)
405 DC power supply and regulator
406 IF output (4800 Vp at 70 kHz)
421 input connector for AC wall outlet voltages 110V/220V at 50 Hz/60 Hz
422 low voltage transformer (LVT)
423 relay system 1 (RS1) for 8 different low voltage levels
424 RL9
425 RL10
426 RL11

427 alpha sine signal inductor Lα
428 beta sine signal inductor Lβ
429 protector circuit
430 high voltage transformer (HVT)
431 negative high voltage (NHV) output
432 positive high voltage (PHV) output
500 schematic of RS1 relay system
510 RS1 relay circuits from RL1 to RL8
511 RS1 6.25V
512 RS2 7.8V
513 RS3 12V
514 RS4 23.5V
515 RS535V
516 RS670V
517 RS7 110V
518 RS8125V
600 HMI screen
601 HS-16000 Vp device logo
610 voltage and duration setting section
611 VLT voltage setting panel
612 Time+ time increase button
613 Time− time decrease function
620 activation panel
621 start button
622 IF voltage selection button
623 preprogrammed treatment
624 Sleep button
625 Wave button
630 wave selection panel
631 network communication
632 sinusoidal selection button
633 alpha wave selection button
634 beta wave selection
641 IoT MCU-1
642 MCU-2
643 relay system (RL1, RL9-RL11)
651 MODBUS
652 network communication (Wi-fi)
700 LC filter
800 relay system (RL1-RL11)
801 RL1
802 RL2
803 RL3
804 RL4
805 RL5
806 RL6
807 RL7
808 RL8
809 RL9
810 RL10
811 RL11
900 IoTCTR relay
910 input AC connector band
911 wall outlet switch band
912 input switching
914 voltage supply jumper
920 IoTCTR
921 110V voltage switching circuit
922 input switch band
923 alpha and beta switching circuit (jumper)
1000 protector circuit
1010 op-am limiting circuit
1020 input selection circuit
1100 IF oscillator circuit (OSC)
1101 negative input
1110 full wave rectifier
1111 oscillator circuit

1200 low voltage transformer (LVT)
1201 negative voltage
1202 L-filter
1213 magnetic coil transformer
1224 negative input voltage
1225 6.25V
1226 10V
1227 18.5V
1228 37V
1229 74V
1230 110V
1231 125V
1240 input selection switching circuit
1300 high voltage transformer (HVT)
1301 out_L
1302 negative voltage
1303 jumper
1304 high voltage transformer
1311 resistive network
1312 positive high voltage (PHV)
1400 MCU1 and USB connector
USB connector circuit
1402 MCU1
1500 RL1 controller
1600 MCU2 and USB connector
MCU2
USB connector
1612 USB controller
1700 DC supply circuit
1800 schematic diagram of parts on the first PCB
PCB traces connecting MCU2 to IoTCTR connector circuit
1802 PCB traces from input connector band to IoTCTR connector circuit
1803 PCB traces from IoTCTR connector circuit to RS1
1804 PCB traces from RS1 to protector circuit
1805 PCB traces from protector circuit to filter
1810 output connector
PCB traces from MCU2 to IF oscillator
1901 wireless communication link
1902 USB connection
1904 PCB traces
1905 PCB traces
PCB power traces
1912 PCB power traces
1913 PCB power traces
2010 first PCB
2020 second PCB
2200 HS-16000 Vp device box
2101 cuboid box
2102 HMI screen
2200 internal PCB boards of the HS-16000 Vp device
2203 main PCB
2221 AC voltage switch
2222 AC input connector
2223 IF output connector
2224 NHV connector
2225 PHV connector
2300 therapeutic waves
2310 pure sine wave
2311 peak of pure sine wave
2120 alpha wave
2121 peak of alpha wave
2130 beta wave
2131 peak of beta wave

What is claimed is:

1. A method for generating electric field therapeutic (EFT) voltages characterized as continuous sinusoidal signals, comprising:

(a) selecting ETF voltages including either IF signals for a first type of treatment or high voltage signals for second type of treatments, wherein said IF signals have preset IF amplitudes and an IF frequency and wherein said high voltage signals have high voltage amplitudes and preset frequencies;

(b) if said IF voltages are selected, then generating said IF signal by generating a reference signal from an oscillator, transforming said reference signal to said IF frequency and said IF amplitudes using a high frequency transformer (HFT), said protecting said If amplitudes using a band pass filter;

(c) otherwise, if said high voltage signals are selected then first transforming an AC wall outlet voltage at 110V/220V with 50 Hz/60 Hz frequency into a plurality of low voltages using a low voltage transformer (LVT); second, selecting one of said plurality of low voltages using respective plurality of relay circuits, wherein each plurality of low voltages is input into corresponding respective said plurality of relay circuits;

(d) transforming said selected plurality of low voltages into either regular sinusoidal signal, an alpha (α) type signal or a beta (β) type signal;

(e) protecting said regular sinusoidal signal, said alpha type signal, and said beta type signal using a current limiting op-amp;

(f) up converting said protected alpha type signal and said beta type signal into either a positive high voltage (PHV) or a negative high voltage (NHV) using a high voltage transformer;

(g) saving said ETF voltages, treatment data, and technical problems in a memory device; and (h) communicating said ETF voltages, said treatment data, and said operation problems to external devices using a second microcontroller (IoTCTR).

2. The method of claim 1 wherein said step (a) further comprises selecting said ETF voltages and treatment durations using an HMI touchscreen electrically coupled to a microprocessor control unit (MCU).

3. The method of claim 2 wherein said HMI touchscreen electrically coupled to said first microprocessor control unit (MCU) by a MODBUS communication.

4. The method of claim 3 wherein said MODBUS communication is RS485 twisted pair electrical cable.

5. The method of claim 1 wherein said IF voltages have a peak-to-peak amplitude of 2800V at a frequency of 70 kHz.

6. The method of claim 1 wherein said high voltage signals comprise 800V, 1000V, 1500V, 3000V, 4500V, 9000V, 14000V, and 16000V at a frequency of 50 Hz/60 Hz.

7. The method of claim 6 wherein said plurality of low voltages comprises 6.25V, 7.8V, 12V, 23.5V, 35V, 70V, 110V, and 125V.

8. The method of claim 7 wherein said second microcontroller (IoTCTR) communicate said ETF voltages, said treatment data, and said operation problems to said external devices using a wireless communication channel.

9. The method of claim 8 wherein said wireless communication channel comprises a Wi-fi communication.

10. The method of claim 9 further comprising retrieving said ETF voltages and said treatment data from said memory device built internal to said first microcontroller.

11. An electrical field therapeutic device, comprising:

a selector for selecting ETF voltages including either IF voltages for a first type of therapeutic treatment or high voltages for a second type of therapeutic treatment, and a treatment duration;

an IF signal generator for generating said IF voltages, wherein said IF generator further comprises an oscillator for generating a sinusoidal signal at a preset IF frequency and a preset IF amplitude and a high frequency transformer (HFT) operative to transform said sinusoidal signal to said IF voltages;

a bandpass filter, electrically coupled to said IF signal generator, operative to protect said IF voltages;

a low voltage transformer for transforming an AC wall outlet voltage of 110V/120V at a respective frequency of 50 Hz/60 Hz into a plurality of low voltages if said high voltages are selected, wherein said low voltage transformer further comprises a switch coupled to select either 110V AC wall outlet voltage or 120V AC wall outlet voltage;

a relay system electrically coupled to select one of said plurality of low voltages in accordance with inputs of said selector;

a high voltage transformer, electrically coupled to said relay system, operative to transform said selected plurality of low voltages to said high voltages;

a protector circuit, electrically coupled to said high voltage transformer, operative to protect said high voltages from distortions;

a first microprocessor operative to communicate said IF voltages corresponding to said first type of therapeutic treatment, said high voltages corresponding to said second type of therapeutic treatment, and said treatment duration;

a second microprocessor, electrically coupled to said selector, operative to control said plurality of relay circuits and store said IF voltages corresponding to said first type of therapeutic treatment and said high voltages corresponding to said second type of therapeutic treatment.

12. The device of claim 11 wherein said selector further comprises an HMI touchscreen that is coupled to said first microprocessor by a MODBUS communication link.

13. The device of claim 12 wherein wherein said MODBUS communication is a RS485 twisted pair electrical cable.

14. The device of claim 13 wherein said first microprocessor is characterized as having a wireless communication capability.

15. The device of claim 14 wherein said wireless communication link is a Wi-Fi.

16. The device of claim 15 wherein said IF signal has a peak-to-peak amplitude of 2800V at a frequency of 70 kHz.

17. The device of claim 16 wherein said high voltages comprises 800V, 1000V, 1500V, 3000V, 4500V, 9000V, 14000V, and 16000V at a frequency of 50 Hz/60 Hz.

18. The device of claim 11 wherein said relay system further comprises a plurality of relay circuits, an alpha (α) inductor, and a beta (β) inductor.

19. The device of claim 18 wherein said protector circuit further comprises a current limiting op-amp.

20. The device of claim 19 wherein said second microprocessor is a RISC based microcontroller with flash memory.

* * * * *